(12) United States Patent
Dorak et al.

(10) Patent No.: US 8,394,587 B2
(45) Date of Patent: Mar. 12, 2013

(54) SINGLE NUCLEOTIDE POLYMORPHISMS AND USE OF SAME PREDICTING MALE-SPECIFIC PRENATAL LOSS

(75) Inventors: Mehmet Tevfik Dorak, Hamilton, NJ (US); Esma Ucisik-Akkaya, Selden, NY (US); Charronne Davis, Mahwah, NJ (US); Thuy Ngoc Do, Hamilton, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 350 days.

(21) Appl. No.: 12/386,106

(22) Filed: Apr. 14, 2009

(65) Prior Publication Data

US 2010/0081135 A1 Apr. 1, 2010

Related U.S. Application Data

(60) Provisional application No. 61/124,111, filed on Apr. 14, 2008, provisional application No. 61/132,634, filed on Jun. 20, 2008.

(51) Int. Cl.
*C12Q 1/68* (2006.01)
*C12P 19/34* (2006.01)

(52) U.S. Cl. ............ 435/6.11; 435/6.12; 435/91.2
(58) Field of Classification Search .......... None
See application file for complete search history.

(56) References Cited

PUBLICATIONS dbSNP record having submitted SNP(ss) details: ss23928476, first entered into dbSNP Aug. 10, 2004, and retrieved from dbSNP on Oct. 18, 2011, two pages.*
By dbSNP Method Detail, method ID AFD_CHIP_HYB, retrieved from dbSNP on Oct. 19, 2011, three pages.*
dbSNP record having submitted SNP(ss) details: ss24169515, first entered into dbSNP Aug. 20, 2004, and retrieved from dbSNP on Oct. 19, 2011, two pages.*
Bergeron RJ., Trends in Biochem. Sci., 1986; 11(133): 133-136.
Boklage CE., Int. J. Fertil., 1990; 35(2): 75-94.
Bombell S., et al., Aust. NZ J. Obstet. Gynaecol., 2008; 48(2): 147-154.
Campbell H., et al., Hum. Mol. Genet., 2007; 16: 233-241.
Carrington M., et al., Science, 1999; 283(5408): 1748-1752.
Christiansen OB., et al., Semin. Reprod. Med., 2006; 24(1): 5-16.
Denic S., et al., JAMA, 2008; 300(2): 169-170.
Denschlag D., et al., Mol. Hum. Reprod., 2004; 10(3): 211-214.
Dorak, MT., et al., Genes Immun., 2002; 3: 263-269.
Dorak, MT., et al., Genes Immun., 2006; 7: 450-467.
Drife JO., British Medical J., 1983; 286: 294.
Goodman C., et al., Fertil. Steril., 2009 (in press).
Hanna J., et al., Nat. Med., 2006; 12: 1065-1074.
Hayashi T., et al., Cancer Res., 2006; 66: 563-570.
Healey CS., et al., Nat. Genet., 2000; 26(3): 362-364.
Hu W., et al., Nature, 2007; 450(7170): 721-724.
Kantarci OH., et al., Arch. Neurol., 2008; 65(3): 349-357.
Kostyu DD., Crit. Rev. Immunol., 1994; 14(1): 29-59.
Lerner SP., et al., Endocr. Rev., 1991; 12(1): 78-90.
Mastenbroek S., et al., N. Engl. J. Med., 2007; 357(1): 9-17.
McMillen MM., Science, 1979; 204(4388): 89-91.
Mincheva-Nilsson L., et al., J. Immunol. 2006; 176(6): 3585-3592.
Ober C., et al., Am. J. Hum. Genet., 1992; 50(1): 6-14.
Pietrowski D., et al., Hum. Reprod., 2005; 20(4): 848-851.
Raulet DH., Nat. Rev. Immunol., 2003; 3(10): 781-790.
Sargent IL., et al., Trends Immunol. 2006; 27(9): 399-404.
Sierra S., et al., Semin. Reprod. Med., 2006; 24(1): 17-24.
Steck T., et al., Eur. J. Obstet. Gynecol. Reprod. Biol., 2004; 112(1): 69-73.
Ucisik-Akkaya E., et al., Tissue Antigens, 2009; 73(2): 177-183.
Vatten LJ., et al., Early Hum. Dev., 2004; 76(1): 47-54.
Zhai W., et al., Mol. Biol. Evol., 2009; 26(2): 273-283.
Ziegler A., et al., Trends Immunol.2005; 26(9): 496-502.
Zhang L., et al., Proc. Natl. Acad. Sci., 1992; 89(13): 5847-5851.
Snabes MC., et al., Proc. Natl. Acad. Sci., 1994; 91(13): 6181-6185.
Coskun S., et al., Prenat. Diagn. 2007; 27(4): 297-302.

* cited by examiner

*Primary Examiner* — Juliet Switzer
(74) *Attorney, Agent, or Firm* — Siu K. Lo

(57) ABSTRACT

The present invention is directed to a panel of single nucleotide polymorphisms (SNPs) in specific genes that serve as biomarkers for sex-specific prenatal loss of a conceptus or embryo. There is provided herein methods and reagents for assessing the specific SNPs in those genes. The method useful in applying these SNPs in predicting an increased risk of prenatal loss is also disclosed.

16 Claims, 5 Drawing Sheets

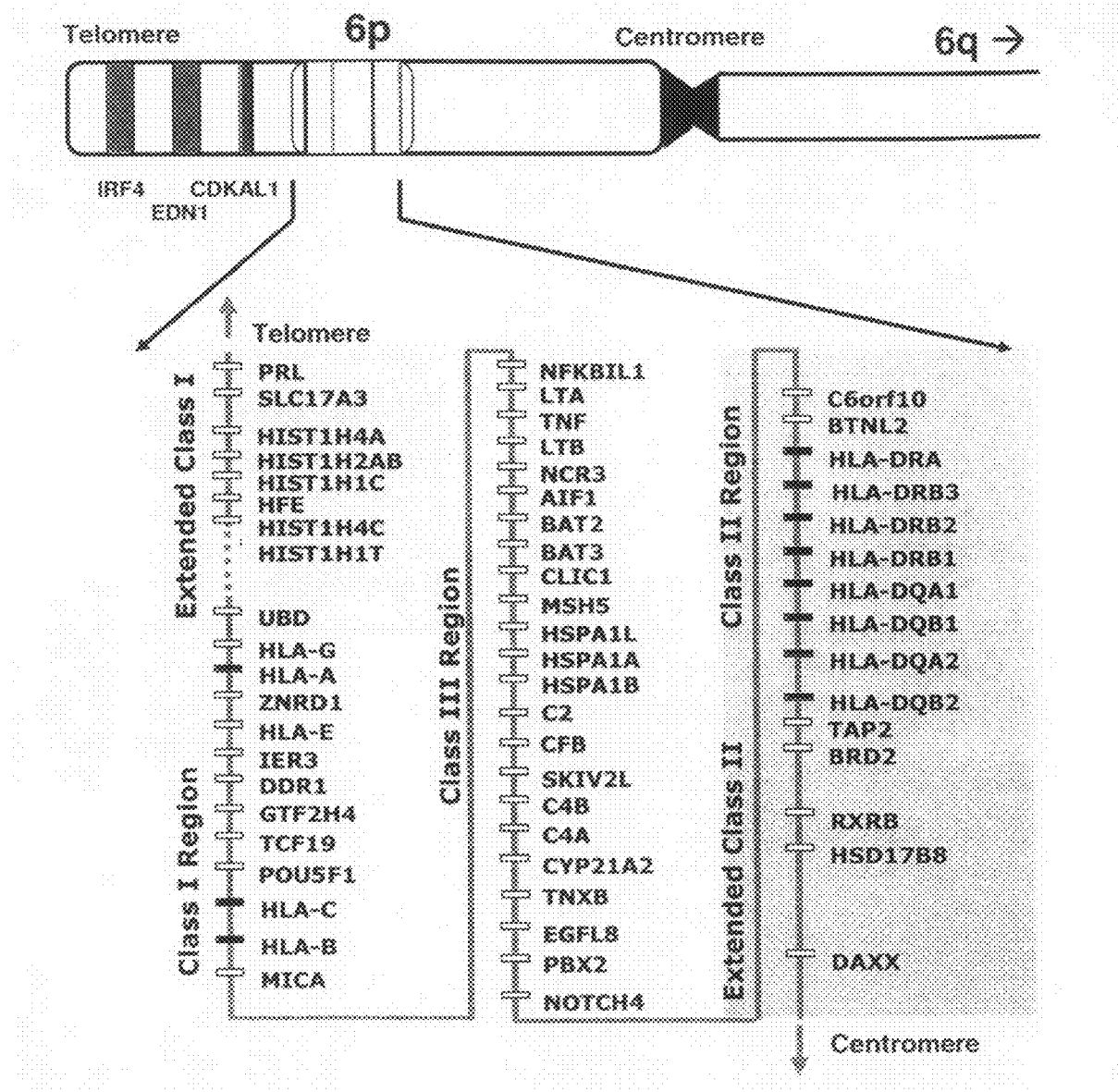

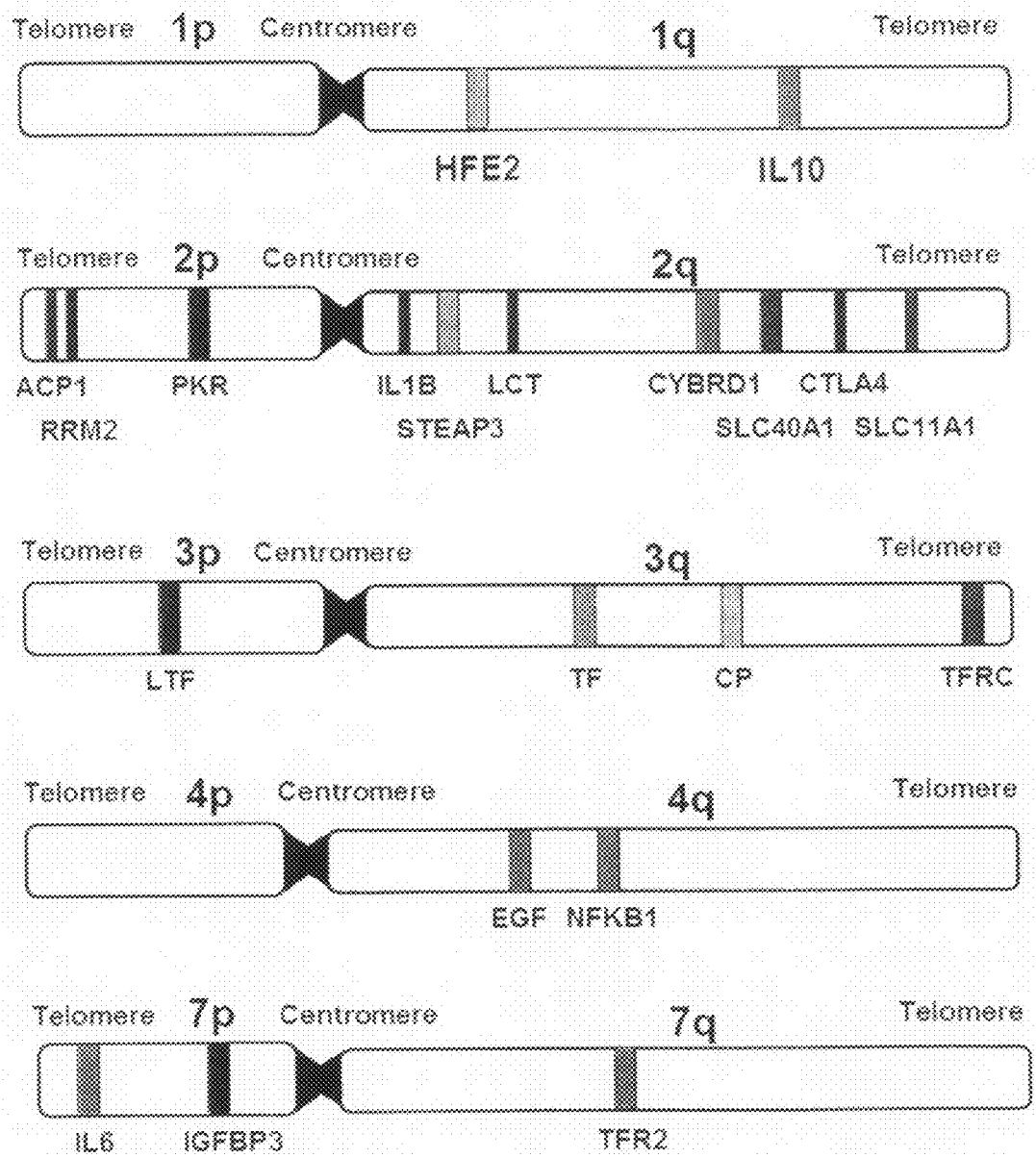

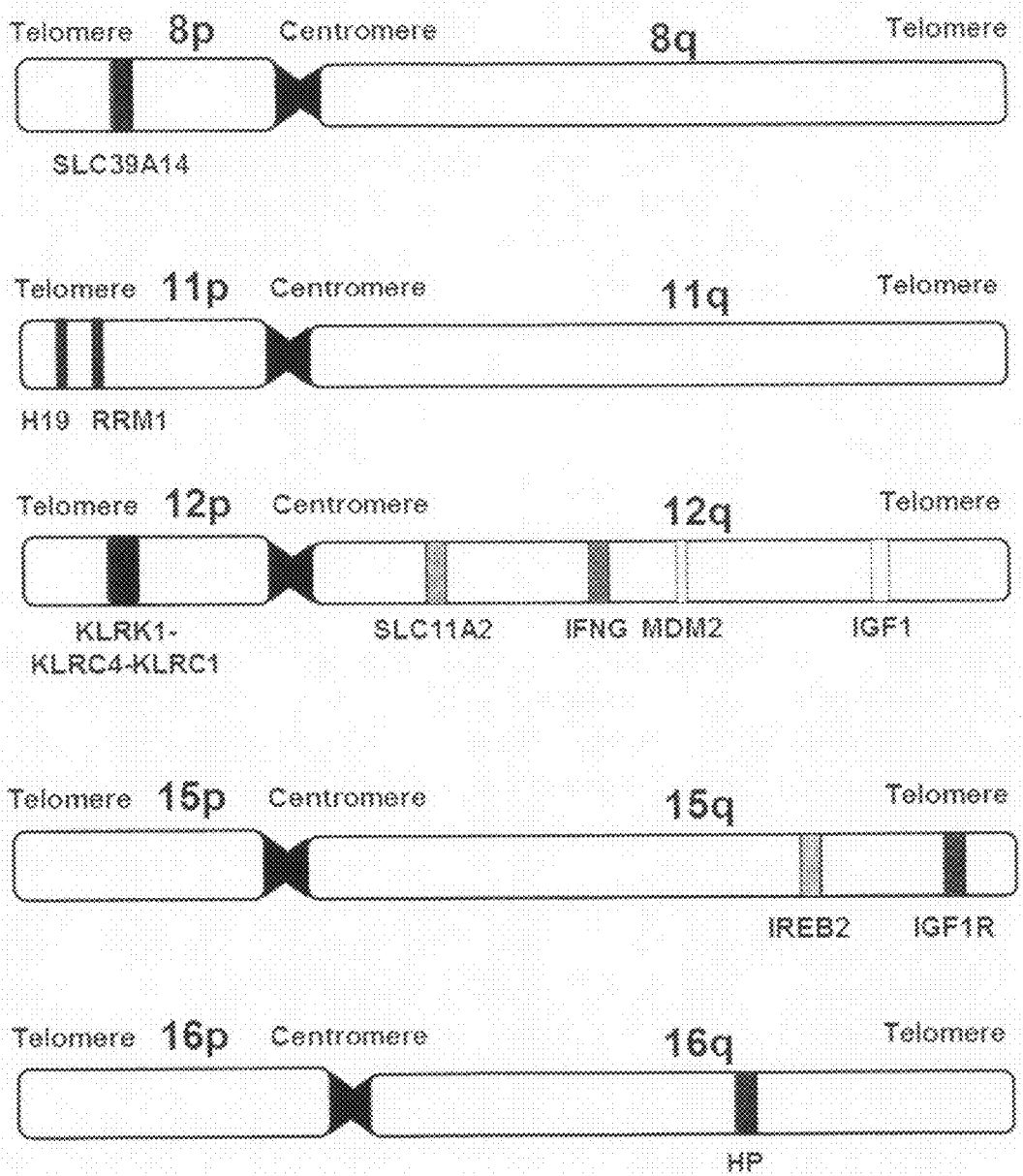

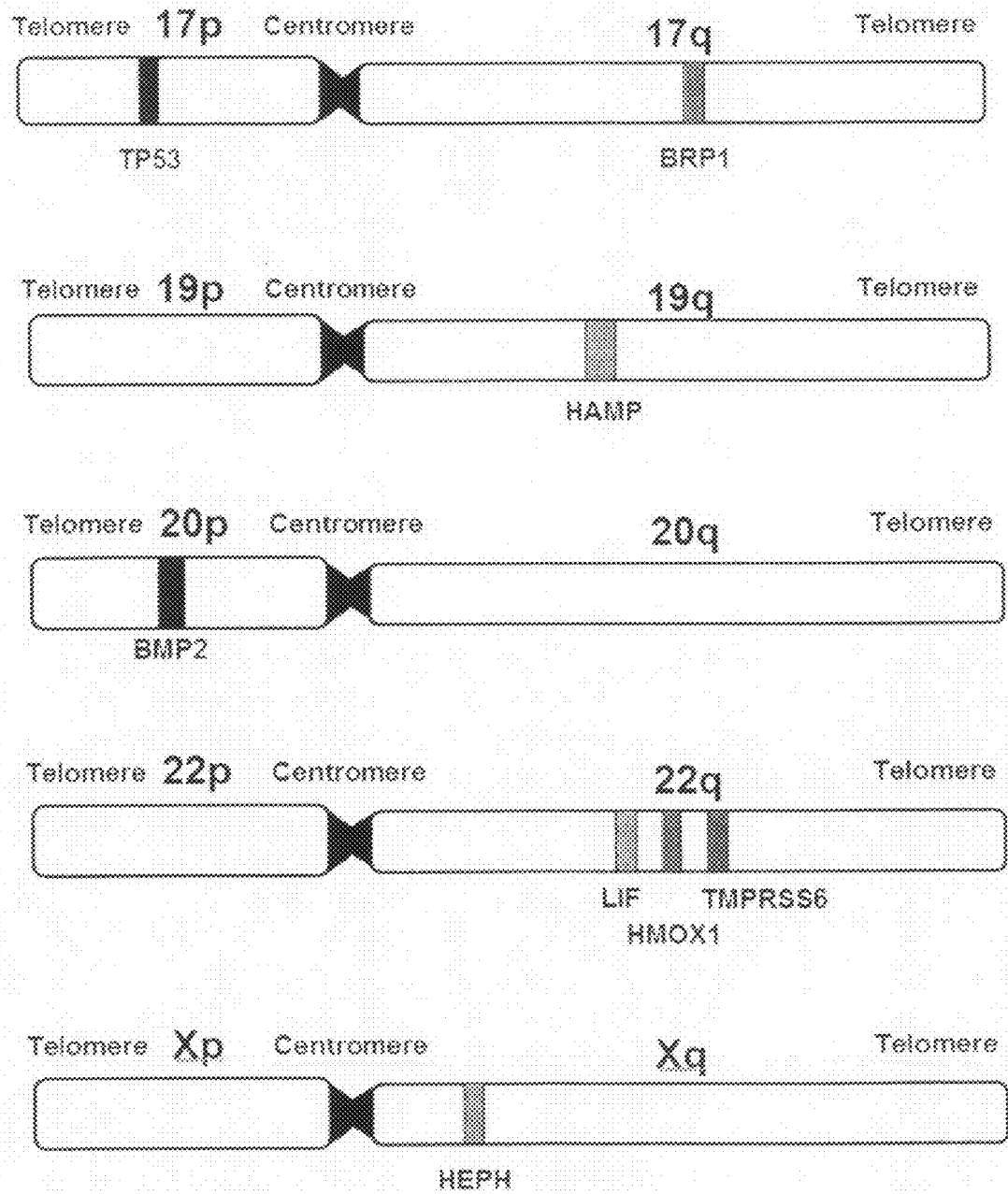

Additive Predictive Value of The Best Subset of Single Nucleotide Polymorphisms As Markers of Prenatal Loss

SINGLE NUCLEOTIDE POLYMORPHISMS AND USE OF SAME PREDICTING MALE-SPECIFIC PRENATAL LOSS

CROSS-REFERENCE TO RELATED APPLICATIONS

This application claims the benefit under 35 U.S.C. §119 (e) to U.S. Provisional Applications Nos. 61/124,111 filed Apr. 14, 2008 and 61/132,634 filed Jun. 20, 2008, the content of which is incorporated by reference herein in their entirety.

BACKGROUND OF THE INVENTION

Prenatal loss is a common occurrence. The survival probability of human conceptions from fertilization to term is estimated to be less than 25% (Roberts & Lowe, 1975). Vatten et al. described a primary male-to-female ratio of 120-165:100 at the time of fertilization, but the ratio decreases to 106:100 at the time of birth. This suggests that prenatal loss concerns males more than that of females, albeit the underlying mechanism is not clear.

There have always been interests and efforts in discovering the contribution of genetic factors to pregnancy loss. A conventional approach is to use population genetics to assess sex-specific prenatal loss. This population genetic approach involves genotyping women experiencing repeated pregnancy loss. Although some positive findings were obtained, the results have been inconsistent. Even if positive findings were obtained, whether miscarriages represent the whole spectrum of repeated pregnancy loss is doubtful. Miscarriages represent only a fraction of the total prenatal loss, and thus rendering the past studies underpowered. Thus, the population genetic approach is suboptimal at best.

Single nucleotide polymorphism (SNP) is a common form of genetic polymorphisms. SNP may influence gene functions and modifies an individual's susceptibility to diseases. Almost any diseases have a genetic component in its etiology and most are being unraveled in genetic association studies. In some instances, a single SNP may be sufficient to confer susceptibility, while in others multiple SNPs may act jointly to influence disease susceptibility. An estimated 20 million SNPs are present in human genome. This astronomical number precludes individual screening one at a time because of the huge work and cost.

To the best of the present inventors' knowledge, there are no reliable genetic markers for prenatal selection (i.e., fetal survival) that have clinical utility. Genetic tests used in in vitro fertilization (IVF) clinics in pre-implantation genetic screening do not contain a genetic marker to predict the survival probability of pregnancy but screens for chromosomal abnormality.

Accordingly, there is a continuing need for a genetic marker to predict the probability of pregnancy success as well as sex-specific prenatal selection. The need for a reliable SNP biomarker for sex-specific prenatal selection is expected to have utility in the application in IVF and infertility clinics.

BRIEF SUMMARY OF THE INVENTION

The present invention is based on the present discovery of particular SNPs in selected genes that represent biomarker candidates in regulating prenatal development for male and female offspring. In accordance with the present invention, the SNPs influence prenatal selection individually or in particular combinations of genotypes, and hence contribute to differential viability of male and female embryos or fetuses.

There is disclosed herein SNPs that contribute to differential viability of male and female embryos or fetuses by their different frequencies in healthy newborn males and females.

In one aspect, the present invention provides a panel of such SNPs that predict sex-specific prenatal selection and methods of using these SNPs in assessing the propensity of prenatal loss probability.

In one aspect, the present invention provides a candidate gene approach and identifying a subset of single nucleotide polymorphisms (SNPs) that is useful to predict the probability of prenatal loss for a given offspring.

In one aspect, the present invention provides a method for predicting prenatal loss of a conceptus or embryo, comprising the steps of: (a) providing a biological sample; (b) isolating nucleic acid from said sample; and (c) assessing the presence of a SNP selected from the group consisting of RXRB rs2076310, HLA-DQA1 rs1142316, HLA-DRA rs7192, HSPA1B rs1061581, GTF2H4 rs3909130, HIST1H1T rs198844, IFNG rs2069727, IL-6 rs1800796, KLRK1 rs10772266, KLRK1 rs2617160, KLRK1 rs2617171, TMPRSS6 rs733655, and HMOX1 rs2071748, wherein the presence of said SNP is indicative of an increased risk of prenatal loss for male conceptus or embryo. Preferably, the biological sample is derived from a conceptus or amniocentesis. The nucleic acid may be genomic DNA, mRNA or isolated DNA.

In one aspect, the present invention provides a method whereby an assessing step for SNPs is performed by polymerase chain reaction-restriction fragment length polymorphism assay or TaqMan allelic discrimination assay. The assessing step is performed preferably by a process which comprises subjecting said nucleic acid to an PCR amplification flanking the region of said SNP.

In one aspect, the present invention provides a method for predicting prenatal loss of a conceptus or embryo by assessing the presence of a combination of SNPs of HLA-DQA1 rs1142316, HLA-DRA rs7192, and HSPA1B rs1061581, wherein the presence of such a combination is indicative of an increased risk of prenatal loss for male conceptus or embryo.

In one aspect, the present invention provides a method of predicting prenatal loss of a conceptus or embryo by assessing the presence of a combination of SNPs of KLRK1 rs10772266, KLRK1 rs2617160, and KLRK1 rs2617171 wherein the presence of such a combination is indicative of an increased risk of prenatal loss for male conceptus or embryo.

In one aspect, the present invention provides a method for predicting prenatal loss of a conceptus or embryo, comprising the steps of: (a) providing a biological sample; (b) isolating nucleic acid from said sample; and (c) assessing the presence of a SNP further selected from the group consisting of RXRB rs421446, BRD2 rs635688, HLA-E rs1264456, IRF4 rs12203592, IRF4 rs872071, LIF rs929271, TP53 rs1042522, MDM2 rs2279744, SLC11A2 rs422982, SLC40A1 rs1439814, and RRM2 rs1130609.

In one aspect, the present invention provides a method for predicting prenatal loss of a conceptus or embryo by assessing the presence of a combination of SNPs of LIF rs929271, TP53 rs1042522, and MDM2 rs2279744, wherein the presence of such a combination is indicative of an increased risk of prenatal loss for male conceptus or embryo.

In one aspect, the present invention provides a method for predicting prenatal loss of a conceptus or embryo by assessing the presence of a combination of SNPs of IRF4 rs12203592, and IRF4 rs872071, wherein the presence of such a combination is indicative of an increased risk of prenatal loss for male conceptus or embryo.

In yet another aspect, the present invention provides a method of predicting prenatal survival probability of a prospective offspring of a couple, comprising the steps of: (a) providing a biological sample; (b) isolating nucleic acid from said sample; and (c) assessing the presence of a SNP selected from the group consisting of RXRB rs2076310, HLA-DQA1 rs1142316, HLA-DRA rs7192, HSPA1B rs1061581, GTF2H4 rs3909130, HIST1H1T rs198844, IFNG rs2069727, IL-6 rs1800796, KLRK1 rs10772266, KLRK1 rs2617160, KLRK1 rs2617171, TMPRSS6 rs733655, and HMOX1 rs2071748, wherein the presence of said SNP is indicative of a decreased prenatal survival probability of a prospective offspring.

In one aspect, the present invention provides a method for predicting a decreased prenatal survival probability of a prospective offspring by assessing the presence of a combination of SNPs of KLRK1 rs10772266, KLRK1 rs2617160, and KLRK1 rs2617171, wherein the presence of such a combination is indicative of a decreased prenatal survival probability of a prospective offspring.

In one aspect, the present invention provides a method for predicting a decreased prenatal survival probability of a prospective offspring of a couple, comprising the steps of: (a) providing a biological sample; (b) isolating nucleic acid from said sample; and (c) assessing the presence of a SNP further selected from the group consisting of RXRB rs421446, BRD2 rs635688, HLA-E rs1264456, IRF4 rs12203592, IRF4 rs872071, LW rs929271, TP53 rs1042522, MDM2 rs2279744, SLC11A2 rs422982, SLC40A1 rs1439814, and RRM2 rs1130609.

In one aspect, the present invention provides a method of predicting a decreased prenatal survival probability of a prospective offspring by assessing the presence of a combination of SNPs of LIF rs929271, TP53 rs1042522, and MDM2 rs2279744, wherein the presence of such a combination is indicative of a decreased prenatal survival probability of a prospective offspring.

In one aspect, the present invention provides a method of predicting a decreased prenatal survival probability of a prospective offspring by assessing the presence of a combination of SNPs of IRF4 rs12203592, and IRF4 rs872071, wherein the presence of such a combination is indicative of a decreased prenatal survival probability of a prospective offspring.

BRIEF DESCRIPTION OF THE DRAWINGS

FIG. 1 depicts the genomic location of the single nucleotide polymorphisms (SNPs) evaluated for their values to predict sex-specific prenatal selection by genotyping healthy newborns.

Figure 2:
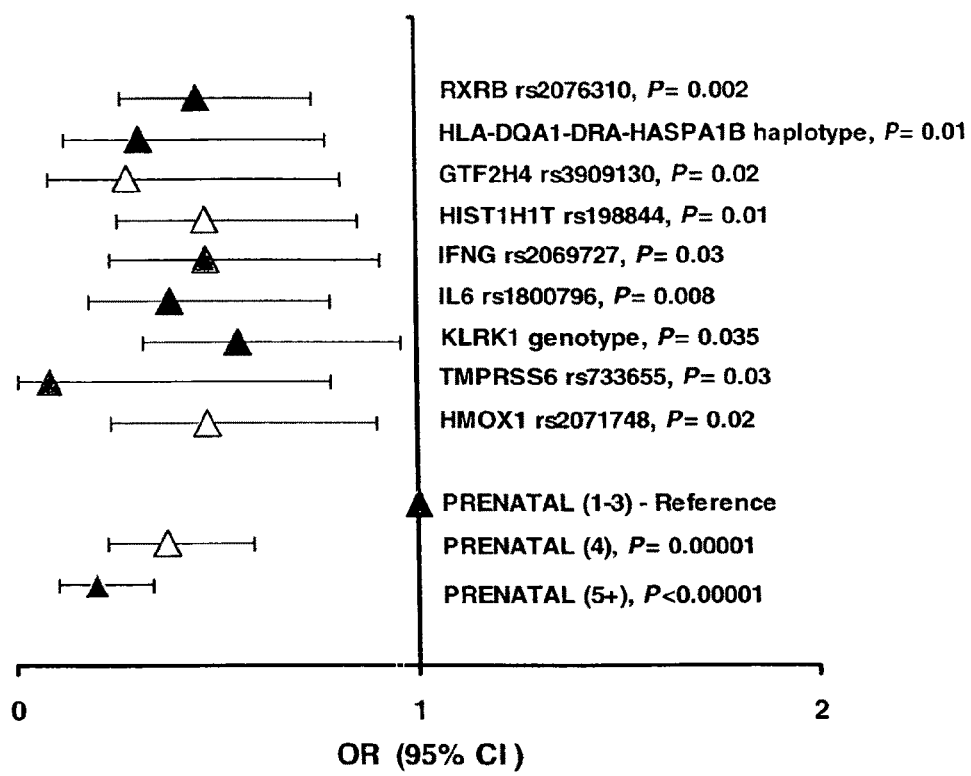
FIG. 2 depicts the individual and additive predictive power of the independent predictive subset of single nucleotide polymorphisms (SNPs) as biomarkers for sex-specific prenatal loss.

On top portion of the figure, individual markers that were found to be independent markers of prenatal loss are shown. At the bottom, the additive effect of having multiple markers is illustrated. When having 1 to 3 markers is used as reference, having 4 markers and having 5 or more markers have increasing effect on male-specific prenatal loss (P value for the cumulative additive effect $<1\times10^{-10}$). The smaller the odds ratio, the more severe the prenatal loss for males.

DETAILED DESCRIPTION OF THE INVENTION

The present inventors cured the prior art deficiency and used a novel approach to identify biomarkers in predicting sex-specific prenatal loss. The present invention provides genetic markers in male and female newborns. The present invention provides comparison of genotype frequencies that provide clues for the involvement of genes in prenatal selection. Selected gene candidate in biologically plausible targets in HLA complex, immune system-related genes (NKG2D and cytokines) and iron-related genes were genotyped in healthy newborns. The present inventors discovered that specific single nucleotide polymorphisms (SNPs) in these genes represent good predictors for sex-specific prenatal selection, and that the prenatal selection acts strongly against male fetuses.

Definitions

Various terms used throughout this specification shall have the definitions set forth herein.

The term "polymorphism" refers to the occurrence of two or more alternative genomic sequences or alleles between or among different genomes or individuals.

The term "polymorphic" refers to the condition in which two or more variants of a specific genomic sequence found in a population.

The term "polymorphic site" is the locus at which the variation occurs. A polymorphic site generally has at least two alleles, each occurring at a significant frequency in a selected population. A polymorphic locus may be as small as one base pair, in which case it is referred to as single nucleotide polymorphism (SNP). The first identified allelic form is arbitrarily designated as the reference, wild-type, common or major form, and other allelic forms are designated as alternative, minor, rare or variant alleles.

The term "genotype" refers to a description of the alleles of a gene contained in an individual or sample.

The term "single nucleotide polymorphism" ("SNP") refers to a site of one nucleotide that varies between alleles.

The term "oligonucleotide" is used interchangeable with "primer" or "polynucleotide."

The term "primer" refers to an oligonucleotide that acts as a point of initiation of DNA synthesis in a PCR reaction. A primer is usually about 15 to about 35 nucleotides in length and hybridizes to a region complementary to the target sequence.

The term "probe" refers to an oligonucleotide that hybridizes to a target nucleic acid in a PCR reaction. Target sequence refers to a region of nucleic acid that is to be analyzed and comprises the polymorphic site of interest.

The term "TaqMan allelic discrimination assay" (also known as the 5' nuclease PCR assay) is a technology that exploits the 5'-3' nuclease activity of Taq DNA polymerase to allow direct detection of the PCR product by the release of a fluorescent report as a result of PCR. The TaqMan allelic discrimination assay permits discrimination between the alleles of a two-allele system. It represents a sensitive and rapid means of genotyping SNPs.

The term "functional SNPs" refers to those SNPs that produce alterations in gene expression or in the expression or function of a gene product, and therefore are most predictive of a possible clinical phenotype. The alterations in gene function caused by functional SNPs may include changes in the encoded polypeptide, changes in mRNA stability, binding of transcriptional and translation factors to the DNA or RNA, and the like.

The term "PCR-RFLP" refers to polymerase chain reaction-restriction fragment length polymorphism. PCR-RFLP is technique to detect a variation in the DNA sequence of a genome by breaking the DNA into pieces with restriction enzymes and analyzing the size of the resulting fragments by gel electrophoresis. PCR-RFLP is one type of genotyping for detecting SNP by visualization of fragments on a gel following restriction endonuclease digestion of the PCR product.

The term "repeated pregnancy loss" is defined clinically as failure of established pregnancies before a live birth more than two times.

The term "an increased risk of prenatal loss" refers to a situation where the survival probability of a male offspring is reduced compared to that of a female. For purposes of this application, it refers to an odds ratio <0.50 (i.e., more than two-fold increased risk) and has a statistically significance of $P \leq 0.05$ indicate strongly increased risk.

The term "95% confidence interval" (or "95% CI") refers to the range of values surrounding the odds ratio (OR) within which the true value is believed to lie with 95% certainty.

The term "conceptus" refers to the embryo in the uterus, during the early stage of pregnancy. The term "embryo" refers an unborn human baby, especially in the first eight weeks from conception, after implantation but before all the organs are developed. For purposes of this application, "conceptus" and "embryo" are used interchangeably.

The term "Hardy-Weinberg equilibrium" refers to a principle that allele and genotype frequencies in a population remain constant; that is, they are in equilibrium-from generation to generation unless specific disturbing influences are introduced. Those disturbing influences include non-random mating, mutations, selection, limited population size, random genetic drift and gene flow. In the simplest case of a single locus with two alleles: one allele is denoted "A" and the other "a" and their frequencies are denoted by p and q; freq(A)=p; freq(a)=q; p+q=1. According to the Hardy-Weinberg principle, when the population is in equilibrium, then we will have freq(AA)=$p^2$ for the AA homozygotes in the population, freq(aa)=$q^2$ for the aa homozygotes, and freq(Aa)=2pq for the heterozygotes.

The term "haplotype tagging SNPs" (htSNPs) refers to a subset of SNPs in each gene that provides sufficient information about genetic variation in a gene as genotyping all of the SNPs in a gene. They basically represent other SNPs in their vicinity and make the others redundant in terms of providing additional information about genetic variation.

The term "linkage disequilibrium" refers to the non-random association in population genetics of alleles at two or more loci. Linkage disequilibrium describes a situation in which some combinations of alleles or genetic markers occur more or less frequently in a population than would be expected from a random formation of haplotypes from alleles based on their frequencies. Non-random associations between polymorphisms at different loci are measured by the degree of linkage disequilibrium.

The term "odds ratio" (OR) refers to the ratio of the frequency of the disease in individuals having a particular marker (allele or polymorphism) to the frequency of the disease in individuals without the marker (allele or polymorphism).

The term "multivariable analysis" refers to an analysis used to assess the independent contribution of each of the multiple risk factors that contribute to a disease condition. That is, multivariable analysis helps to determine the most informative minimal set of independent (uncorrelated) multiple risk markers (variables). In situations where two SNPs from the same gene show statistically significant association, but when tested together in a multivariable analysis, if they are correlated, one of them loses significance and the other one is called an independent marker. The one that is no longer significantly associated is still useful in estimation of the risk in the absence of any other marker, but its association is only due to its correlation with a stronger marker. Since human diseases are often influenced by multiple genes, it is usual to find associations with many SNPs from many genes. In this case, a multivariable analysis is used to eliminate any redundancy.

The term "adjusted odds ratio" refers to an odds ratio that is adjusted with another factor (e.g., age). When all independent risk markers are analyzed together in a multivariable analysis, the odds ratio for each marker may be slightly different from the odds ratios obtained from analysis of each SNP on its own. These new odds ratios are called adjusted odds ratios. Since no SNP acts on its own in reality, these adjusted odds ratios represent a more realistic estimate of the risk. These are odds ratios calculated by statistical algorithms that take into account individual contributions of any other risk marker (variable) included in the multivariable analysis.

In one embodiment, the present invention provides a panel of SNPs that exhibit associations with sex-specific prenatal selection. The SNPs identified are present in specific candidate genes. In another embodiment, the present invention provides a method of using genotyping approach to identify a panel of SNPs listed in Table 4 out of all the 244 SNPs listed in Table 1.

In accordance with the present invention, one of a skilled artisan understands that SNPs have two alternative alleles, each corresponds to a nucleotide that may exist in the chromosome. Thus, a SNP is characterized by two nucleotides out of four (A, C, G, T). An example would be that a SNP has either allele C or allele T at a given position on each chromosome. This is shown as C>T or C/T. The more commonly occurring allele is shown first (in this case, it is C) and called the major, common or wild-type allele. The alternative allele that occurs less commonly instead of the common allele (in this case, it is T) is called minor, rare or variant allele. To avoid confusion, in this patent application, we adopted to use wild-type and variant allele to define the common and rare alleles. Since humans are diploid organisms meaning that each chromosome occurs in two copies, each individual has two alleles at a SNP. These alleles may be two copies of the same allele (CC or TT) or they may be different ones (CT). The CC, CT and TT are called genotypes. Among these CC and TT are characterized by having two copies of the same allele and are called homozygous genotypes. The genotype CT has different alleles on each chromosome and is a heterozygous genotype. Individuals bearing homozygote or heterozygote genotypes are called homozygote and heterozygote, respectively.

The present inventors discovered that by examining genotype frequencies of polymorphisms in newborns, clues may be obtained as to which genes are involved in prenatal loss. This can be achieved by comparing genotype frequencies in newborn males and females for sex-specific selection.

In one embodiment, the present invention provides a method of using genotype data rather than sequence data, SNPs are identified to support the findings in the association study. Hardy-Weinberg equilibrium (HWE) and Ewens-Watterson (E-W) tests are used in the present genotype-based tools to search evidence for selection.

HWE tests check the agreement between observed genotype frequencies and expected frequencies calculated from observed allele frequencies. A perfect agreement is expected when several assumptions are met. One of the assumptions is the absence of selection. A statistically significant result in the goodness-of-fit test examining the agreement suggests disequilibrium. The cause for this is change in genotype distribution in the population is usually selection. In practice, however, the most common cause for Hardy-Weinberg disequilibrium is genotyping errors. It is often possible to distinguish between selection and genotyping error when HWE is violated. Genotyping errors are unlikely to be selective. This means if HWE is violated in males but not in females, it points out towards a selective event that has occurred exclusively in males.

In one embodiment, the present invention provides of method of using a statistical test (e.g., HWE) to obtain evidence for sex-specific prenatal selection using genotype frequencies in male and female newborns. The statistical tests for HWE often yield significant results. The present invention also provides other statistical tests (e.g., E-W test) to complement the HWE test. One of ordinary skill in the art would recognize that detail of the HWE test is publicly available in Haploview version 4.0 (http://www.broad.mit.edu/mpg/haploview).

In one embodiment, the present invention provides another statistical test (i.e., E-W test) that can be used when population genetic data is available. E-W test shares some common feature as that of HWE test. When the E-W test attains a statistically significance, it is an indication of selection. Besides association tests, the present inventors tested the data with both HWE and E-W tests in order to obtain additional evidence for prenatal selection in genotype data generated from healthy newborns. For the E-W test, a publicly available PopGen software version 1.32 (http://www.ualberta.ca/~fyeh) is used.

In accordance with the present invention, there is disclosed an optimal approach that utilizes genotyping to provide direct evidence for sex-specific prenatal loss. In this approach, if a genotype has a deleterious effect on the prenatal development of a male offspring, newborn males will have a reduced frequency for that genotype compared with female newborns. The present approach has advantages of examining healthy newborns who survived the prenatal selection till the end of pregnancy, thus providing summary data regarding all forms of prenatal selection (i.e., implantation failure, embryonic development errors, and fetal loss). The present approach is therefore superior to other approaches (e.g., population genetics) in prenatal selection that focuses on miscarriages. Studying couples experiencing repeated pregnancy loss to find genetic markers is disadvantageous because miscarriages represent a minority of total prenatal loss.

In one embodiment, the present invention provides a method of utilizing an individual SNP to predict susceptibility to prenatal loss of males. In accordance with the present invention, the assessing techniques to determine the presence of a SNP are known in the field of molecular genetics. Further, many of the methods involve amplification of nucleic acids. (See, PCR Technology: Principles and Applications for DNA Amplification (Ed. H. A. Erlich, Freeman Press, NY, N.Y., 1992), and Current Protocols in Molecular Biology, Ausubel, 1999).

In one embodiment, the detection of the presence of a SNP in a particular gene is genotyping. One of the many suitable genotyping procedures is the TaqMan allelic discrimination assay. In this assay, one may utilize an oligonucleotide probe labeled with a fluorescent reporter dye at the 5' end of the probe and a quencher dye at the 3' end of the probe. The proximity of the quencher to the intact probe maintains a low fluorescence for the reporter. During the PCR reaction, the 5' nuclease activity of DNA polymerase cleaves the probe, and separates the dye and quencher. Thus resulting in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

Genotyping is performed using oligonucleotide primers and probes. Oligonucleotides may be synthesized and prepared by any suitable methods (such as chemical synthesis), which are known in the art. Oligonucleotides may also be conveniently available through commercial sources. One of the skilled artisans would easily optimize and identify primers flanking the gene of interest in a PCR reaction. Commercially available primers may be used to amplify a particular gene of interest for a particular SNP. A number of computer programs (e.g., Primer-Express) is readily available to design optimal primer/probe sets. It will be apparent to one of skill in the art that the primers and probes based on the nucleic acid information provided (or publically available with accession numbers) can be prepared accordingly.

The labeling of probes is known in the art. The labeled probes are used to hybridize within the amplified region during the amplification region. The probes are modified so as to avoid them from acting as primers for amplification. The detection probe is labeled with two fluorescent dyes, one capable of quenching the fluorescence of the other dye. One dye is attached to the 5' terminus of the probe and the other is attached to an internal site, so that quenching occurs when the probe is in a non-hybridized state.

As appreciated by one of skill in the art, other suitable genotyping assays may be used in the present invention. This includes hybridization using allele-specific oligonucleotides, primer extension, allele-specific ligation, sequencing, electrophoretic separation techniques, and the like. Exemplary assays include 5' nuclease assays, molecular beacon allele-specific oligonucleotide assays, and SNP scoring by real-time pyrophosphate sequences.

Determination of the presence of a particular SNP is typically performed by analyzing a nucleic acid sample present in a biological sample obtained from an individual. Biological sample is derived from a conceptus or amniocentesis. The nucleic acid sample comprises genomic DNA, mRNA or isolated DNA. The nucleic acid may be isolated from blood samples, cells or tissues. Protocols for isolation of nucleic acid are known. When RNA is used, the analysis can be performed by first reverse-transcribing the target RNA using, for example, a viral reverse transcriptase, and then amplifying the resulting cDNA.

PCR-RFLP represents an alternative genotyping method used in the invention. PCR-RFLP can yield unambiguous results provided that there is a suitable endonuclease that will cut the amplified PCR product containing a SNP if it contains one of the alternative nucleotides but not the others. Results of PCR-RFLP may be achieved by visualization of fragments on a gel following restriction endonuclease digestion of the PCR product. Thus, a fragment of DNA containing the SNP is first amplified using two oligonucleotides (primers) and is subject to digestion by the variant allele-specific restriction endonuclease enzyme. If the fragment contains the variant allele it is cut into two or more pieces and in the absence of the variant allele, the PCR product remains intact. By visualizing the end-products of the digestion process by agarose or polyacrylamide gel electrophoresis, the presence or absence of the variant allele is easily detected. Other suitable methods that are known in the art such as single-base extension assay, oligonucleotide ligation assay, DNA microarray, pyrosequencing, high-resolution melting method, denaturing high-performance liquid chromatography, mass spectrometry, microsphere-based suspension array platform (Luminex)-based assays and the like can be used in the present invention to detect the presence of SNP.

In one embodiment, the present invention provides a panel of individual SNPs that are useful in predicting sex-specific prenatal loss. This panel of SNPs includes RXRB rs2076310, HLA-DQA1 rs1142316, HLA-DRA rs7192, HSPA1B rs1061581, GTF2H4 rs3909130, HIST1H IT rs198844, IFNG rs2069727, IL-6 rs1800796, KLRK1 rs10772266, KLRK1 rs2617160, KLRK1 rs2617171, TMPRSS6 rs733655, and HMOX1 rs2071748.

In another embodiment, the present invention further provides an additional panel of individual SNPs useful in predicting sex-specific prenatal loss. This additional panel includes RXRB rs421446, BRD2 rs635688, HLA-E rs1264456, IRF4 rs12203592, IRF4 rs872071, LIF rs929271, TP53 rs1042522, MDM2 rs2279744, SLC11A2 rs422982, SLC40A1 rs1439814, and RRM2 rs1130609.

In another embodiment, the present invention provides a method of utilizing multiple SNPs that would exert joint effects and alter the individual's susceptibility to sex-specific prenatal loss.

In one embodiment, the present invention provides a method of using haplotype tagging SNPs (i.e., htSNPs). hsSNPs represent a cluster of SNPs in their vicinity; together, they provide additional information about genetic variation. The present invention provides a method of using the htSNP approach. When there is no already known functional SNP available in a candidate gene, the present invention provides a method of using htSNPs to predict individual's susceptibility to sex-specific prenatal loss. The goal is to use functional SNPs that are known to affect either the function or expression of a gene. The use of functional SNPs may yield a positive association. On the other hand, a non-functional SNP may also be a marker to predict the outcome.

Haplotype tagging SNPs are capable of representing other SNPs. This is because of a phenomenon called linkage disequilibrium (LD). An htSNP and other SNPs tagged or represented by the htSNP form a group that are equally informative when genotyped individually. Any pair of SNPs that are in linkage disequilibrium may provide the same information. If one SNP is associated with a disease condition, the other SNP is similarly associated with the same disease condition. This generates a situation in genetic association studies where an association may be replicated by using a different SNP that is in the linkage disequilibrium with the original SNP. Accordingly, the SNPs in the present panel may be replaced by other SNPs to yield the same information. The linkage disequilibrium information is available in public resources such as HapMap (http://www.hapmap.org) or genome variation server (GVS: http://gvs.gs.washington.edu/GVS).

In one embodiment, the present invention provides a panel of SNPs, when in combination, produces a synergistic effect on sex-specific prenatal loss. While an individual SNP alone has no effect, the combined SNPs together exert a significant effect. In an exemplary embodiment, the presence of a combination of SNPs of HLA-DQA1 rs1142316, HLA-DRA rs7192, and HSPA1B rs1061581 is indicative of a sex-specific prenatal loss. In another exemplary embodiment, the presence of a combination of SNPs of KLRK1 rs10772266, KLRK1 rs2617160, and KLRK1 rs2617171 is indicative of a sex-specific prenatal loss.

In yet another exemplary embodiment, the presence of a combination of LIF rs929271, TP53 rs1042522, and MDM2 rs2279744 is indicative of a sex-specific prenatal loss. In another exemplary embodiment, the presence of a combination of SNPs of IRF4 rs12203592, and IRF4 rs872071 is indicative of a sex-specific prenatal loss.

The SNP's individual and combined effects on sex-specific prenatal loss against male are similar to that in decreasing prenatal survival probability of a prospective offspring.

As will be apparent to one of skill in the art, one utility of the present invention relates to the field of in vitro fertilization (IVF). After a fertilized egg undergoes cell division to become multiple cell stages (i.e., 8-cell stage), the cells can be separated. The single cell can be used to perform multiple genotyping. This can be achieved by whole genome amplification (WGA). The technology for amplifying DNA from a single cell is known. The resulting whole genome amplified DNA can be used for PCR-based genotyping. The use of WGA in pre-implantation genetic testing on single cell biopsies from 8-cell stage embryo is known in the art. (See, e.g., Zhang et al. Proc. Natl. Acad. Sci. USA 89(13): 5847-51 (1992), Snabes et al., Proc. Natl. Acad. Sci. USA 91(13): 6181-5 (1994), and Coskun et al., Prenat. Diagn. 27(4): 297-302 (2007). After the genotyping assessment of the presence of specific SNPs, a physician can thereby predict the risk of sex-specific prenatal loss or chance of prenatal survival probability of a prospective offspring. The present invention provides a useful tool in deciding to implant a particular fertilized embryo based on the genotyping results.

EXPERIMENTAL STUDIES

Example 1

Characteristics of Population Samples

To obtain evidence for sex-specific prenatal selection, we examined genotype frequencies in male and females newborns and compared these frequencies for differences by statistical methods. Any difference found suggested differential viability for male and female fetuses bearing that genotype.

The population samples consisted of 388 cord blood samples form 201 girls and 187 boys. The cord blood samples were collected in EDTA-containing tubes. White blood cells were isolated using standard protocols. DNA was extracted from white blood cells using standard phenol-chloroform extraction method or equivalent methods. DNA samples were re-suspended in double distilled $H_2O$ at 100 nanograms per microliter and kept frozen at $-20°$ C. until used for genotyping. Further details of the samples are provided in detailed experimental procedures section.

Table 1 lists all of the 244 SNPs from the candidate genes we selected to test for their predictive value for prenatal selection. The table provides the gene name, the SNP ID number (beginning with rs) as listed in National Center for Biotechnology Information (NCBI) Entrez SNP (http://www.ncbi.nlm.nih.gov/sites/entrez?db=snp), chromosomal location and the position in the chromosome as nucleotide number beginning from the tip of the short arm of a chromosome.

Each one of the 244 SNPs from our candidate genes were genotyped in newborns and genotype frequencies were compared between male and female newborns. Any difference between the frequencies was considered to be an indication of differential viability of male and female offspring.

Example 2

Selection of Genes for Testing their Role in Prenatal Selection

To the best of the present inventors' knowledge, despite few published reports (Healey et al., 2000; Denschlag et al., 2004; Pietrowski et al., 2005; Goodman et al., 2009), there are no genetic polymorphisms for prediction prenatal selection (i.e., fetal survival) in clinical use. Past studies designed to correlate genetic markers to prenatal selection using couples who had experienced recurrent miscarriages. However, these miscarriages represent only a fraction of the total prenatal loss, and thus rendering the past studies underpowered.

The present inventors used a new approach. We noted that male-to-female ratio is high at the time of fertilization in humans; however, the male-to-female ratio diminishes by the time of birth (i.e., from up to 165 males-to-100 females to 106 males-to-100 females). We postulated and tested the hypothesis that prenatal selection is sex-specific; that is, prenatal selection acts strongly against male fetuses. To test this hypothesis, we examined genetic markers in male and female newborns.

While any gene may have a role in embryonic or fetal viability, we stratified the genes for the probability of their involvement in prenatal selection and used a candidate gene approach. Besides known physiologic roles of genes, we also exploited our own findings in childhood leukemia since susceptibility to leukemia and prenatal selection share genetic risk markers. Furthermore, childhood leukemia is more common in males and since we explored markers for sex-specific prenatal selection, we included leukemia risk markers. Most of these markers are from the HLA complex and iron regulatory genes but also included selected cytokine genes IFNG, IL-10, IL-6 and LIF (See, Table 1 and FIG. 1). These two groups of genes represent plausible gene candidates for prenatal selection.

We chose to examine additional gene candidates. These include heme oxygenase I (i.e., HMOX1), leukemia inhibitory factor (i.e., LIF) and natural killer cell receptor (i.e., NKG2D). We analyzed selected polymorphisms of these relevant genes in the potential genetic marker list (See, Table 1, and FIG. 1).

Furthermore, we examined selected polymorphisms of TP53, IL-6, IL-10, IL-1β. These genes have been suggested to associate with prenatal selection (TP53) and repeated pregnancy loss (HMOX1, IL-6, IL-10, IL-1β).

Example 3

Genotypings of Single Nucleotide Polymorphisms

Genotypings of SNPs were achieved by a variety of methods. They usually provide equivalent results. The choice was based on availability of the necessary instruments and expertise, budget available for the study and convenience. Our choice of method was TaqMan allelic discrimination assay for ordinary SNP genotyping. All TaqMan assays were purchased from ABI (California) (See Table 6).

When TaqMan allelic discrimination assay was not possible to use, we chose an alternative method. This happened for MDM2 rs2279744, HSPA1B rs1061581 and HLA-DQA1 rs1142316. For these polymorphisms, we used a PCR based restriction fragment length polymorphism assay. The details of these methods used to genotype polymorphisms within our candidate genes are given in the detailed experimental procedures section.

Table 2 shows the 24 SNPs either showed an individual difference in genotype frequencies between male and female healthy newborns or contributed to a combination of regional genotype combinations that showed frequency differences. The gene name, SNP ID number, alternative name for the SNP according to Genome Variation Society (HGV), when available, SNP location within the gene and nucleotide change are shown.

Example 4

Natural Killer Cell Receptor KLRK1 (NKG2D) and Prenatal Loss

The major role played by NK cells in maternal tolerance to fetus is well recognized (Sargent et al, 2006; Hanna et al, 2006). It has been shown that maternal immune tolerance to developing offspring, which is immunologically foreign to maternal immune system, is achieved by natural killer cells. Natural killer cell activity is regulated by multiple molecules and receptor systems. Among those, the most powerful is the NKG2D receptor encoded by the KLRK1 gene (Raulet DH, 2003). The KLRK1 gene is polymorphic and these polymorphisms are associated with cancer susceptibility (Hayashi et al, 2006).

We obtained genotype and allele frequencies in the healthy newborns. In overall analysis, all loci were in HWE with the exception of rs10772266 (P=0.004) and in sex-specific analysis, this distortion was evident in boys only (P=0.02) suggesting a selection event affecting males during prenatal period. In most other SNPs, HWE was mildly violated in boys (rs1049174, rs2617160, rs2617170, rs2617171) while all SNPs remaining in equilibrium in girls. The E-W neutrality test showed statistically significant evidence for selection only for rs10772266 and only in boys.

The same KLRK1 haplotype that was described as associated with low natural cytotoxic activity in Japan (Hayashi et al, 2006) was the commonest haplotype also in the Caucasian sample analyzed here. Notably, all the SNPs within the haplotype block described by Hayashi et al. showed differences between boys and girls in their frequencies. Inspection of genotype frequencies revealed that there were differences in heterozygous frequencies between boys and girls and boys had consistently lower rates for heterozygous genotypes. The stronger violation of HWE in boys suggested that selection was stronger in boys and the statistical assessment showed that the deviation was heterozygote deficit in boys rather than excess in girls.

The magnitude of deficit in boys was 18.4% for rs2617170, which is a coding region variant (N104S) in KLRC4 immediately 3' to the KLRK1 gene. This variant is also an htSNP for the 3' end of KLRK1 in the HapMap project. Since the sample was healthy newborns, we interpreted this finding as suggestive evidence for the involvement of KLRK1 in feto-maternal interactions and possibly in sex-specific prenatal selection. The strong evidence for a functional role played by KLRK1 in feto-maternal interactions is the demonstration of the secretion of soluble MHC class I chain-related molecules (MIC) by placental trophoblastic cells to counteract the maternal NK cell activity by blocking KLRK1 receptors.

Example 5

Genetic Markers in HLA-Complex that Correlate with Prenatal Selection

We identified three genetic markers that bear high correlation with prenatal selection in homozygosity representing main lineages of HLA haplotypes. These genetic markers are: (i) HSPA1B rs1061581; (ii) HLA-DRA rs7192; and (iii) HLA-DQA1 rs1142316. The major alleles of these SNPs characterize the ancestral HLA-DRB4 lineage (i.e., HLA- DR4, HLA-DR7 and HLA-DR9). The minor alleles of these SNPs characterize the HLA-DRB3 lineage (i.e., HLA-DR3, HLA-DR11/12 and HLA-DR13/14). The frequency in male newborns who were homozygote for either the major alleles or minor alleles of the three SNPs was 5.9%. In contrast, the frequency in female newborns was 14.6%. The comparison between the frequencies in male and female newborns was statistically significant (P=0.006). The more than two-fold deficit in homozygosity of SNPs in male newborns is consistent with the hypothesis that there exists a prenatal selection against male offspring bearing these SNP haplotypes.

We hypothesized that transcription factors encoded within the HLA complex may also be relevant in prenatal selection. There are several embryo-expressed and evolutionarily conserved transcription factor genes within the HLA complex. Of these, SNPs from RXRB, BRD2 and GTF2H4 showed statistically significant frequency differences between male and female newborns and RXRB2 and GTF2H4 retained their significance in the multivariable model as independent markers of prenatal selection. Besides these, HLA-E and HIST1H1T also showed frequency differences between males and females with HIST1H1T remaining in the final model (these results are presented in Tables 3 and 4).

Example 6

Iron-Related Gene Polymorphisms and that Correlate with Prenatal Selection

Iron is a required element for cellular proliferation. One iron-related gene HMOX1 (heme oxygenase 1) has been shown to affect recurrent miscarriage susceptibility (Denschlag et al., 2004). This association was, however, with a promoter region microsatellite marker, which is not as easy to type as a SNP marker. We studied the HMOX1 gene SNPs to search associations with prenatal selection.

The SNP rs2071748 showed a sex-specific frequency difference in newborns. The frequency in male newborns who were homozygote for the minor allele of rs2071748 was 14.7%. In contrast, the frequency in female newborns was 22.1%. The difference between the frequencies in male and female newborns reached borderline statistical significance (P=0.06). The ~two-fold deficit in homozygosity of the SNP in male newborns is consistent with the hypothesis that there is a prenatal selection against male fetuses bearing this SNP genotype.

The present inventors screened iron regulatory pathway genes and detected associations with sex-specific prenatal loss (OR$\leq$0.67 or P$\leq$0.05). These SNPs were from the genes SLC11A2 (also known as NRAMP2), SLC40A1, RRM2 and TMPRSS6. The SNPs and accompanying statistics are listed in Table 3.

Example 7

Leukemia Inhibitory Factor (LIF) and Sex-Specific Prenatal Selection

We examined LIF and its natural genetic variation to search for variants as markers for prenatal loss. LIF interacts with TP53 and TP53 interacts with MDM2. We found functional polymorphisms of TP53 its interaction with MDM2 to produce joint effects.

Individually LIF, TP53 and MDM2 SNPs did not show a statistically significant association with sex-specific prenatal loss. The only suggestive association was with wild-type homozygosity for the LIF SNP rs929271, which yielded an odds ratio of 0.71 (P=0.10). However, when all three SNPs were analyzed together, there was a significant finding. The combination of having wild-type homozygote genotypes in each of the three SNPs at LIF, TP53 and MDM2 showed a deficit in newborn males compared with girls (OR=0.30, 95% CI=0.12 to 0.75; P=0.009). This finding confirmed the involvement of LIF in the success of pregnancy and also the interactions with TP53/MDM2 as expected form their biologic interaction. The present investigation showed the sex-specificity of this effect in that having the wild-type homozygote genotypes at these three SNPs has a deleterious effect for male offspring and such offspring have three-times reduced chance of reaching the end of pregnancy.

Example 8

Associations of Cytokine Genes Interferon-Gamma (IFNG) and Interleukin-6 (IL-6) Polymorphisms with Sex-Specific Prenatal Loss We examined IFNG SNP in our candidate SNPs because of its sex-specific expression patterns. To investigate their association with sex-specific prenatal selection, we genotyped selected SNPs from IL-6, IL-10 and IFNG genes. Two of those, IFNG rs2069727 and IL-6 rs1800796, showed different genotype frequencies between male and female newborns. These results are shown in Table 3. The effect of these SNPs was strong enough to remain in the multivariable model in the presence of other markers of prenatal loss. The adjusted odds ratios were less than 0.50 for both SNPs (Table 4) meaning reduced chance of survival for male offspring during pregnancy.

Example 9

Heterozygote Advantage in Sex-Specific Prenatal Selection

In this series of study, we examined heterozygosity at all SNPs for its effect on sex-specific prenatal selection. As already mentioned in different sections above, HLA-E rs1264456 individually, IRF4 SNPs rs12203592 and rs872071 in combination, and KLRK1 SNPs rs2617160 and rs2617171 in combination showed reduced frequencies in male newborns compared with female newborns. The HLA-E and IRF4 SNPs were not retained in the final model but the two KLRK1 region SNPs in combination with rs10772266 remained statistically significant.

Altogether, the present inventors discovered genetic markers including KLRK1 region, individual HLA complex genes, cytokine genes, HMOX1 and other iron regulatory genes as predictors in sex-specific prenatal selection.

Example 10

Prediction of Propensity to Prenatal Loss: Individual SNP Analysis

Individually, RXRB rs421446, RXRB rs2076310, BRD2 rs635688, GTF2H4 rs3909130, HIST1H1T rs198844, SLC11A2 rs422982, SLC40A1 rs1439814, RRM2 rs1130609, IFNG rs2069727 showed frequency differences between males and females for wild-type allele or variant allele positivity (dominant genetic model). This is interpreted as being positive for a certain allele of these SNPs was unfavorable for male offspring and they were less likely to reach the end of pregnancy. As the odds ratios lie between 0.37 and 0.67, male offspring bearing any of these genotypes have at least 33% reduced chance of surviving pregnancy.

As will be seen in Table 3, some genotypes did not reach statistical significance using the conventional criterion (P≦0.05) but they are still listed if the association was marginally significant (P=0.06 to 0.10) and odds ratios were 0.67 or smaller. This was only done to be able to assess those SNPs in the multivariable models (in which they may reach statistical significance because of their small odds ratios).

Two RXRB SNPs reached statistical significance in their association with prenatal loss. When this happens, it is customary to examine their independence from each other because most common reason for this is that the two SNPs are correlated. In genetic data analysis, this means they are in linkage disequilibrium (LD). An examination of LD between RXRB SNPs rs421446 and rs2076310 showed extremely significant correlation (correlation coefficient=0.81, P<$10^{-10}$). Multivariable modeling showed that the primary association was with rs2076310 and the other SNP showed an association simply because of its LD with rs2076310. Consequently, only RXRB rs2076310 was considered for further analysis in the next step (multivariable modeling).

TMPRSS6 rs733655, HMOX1 rs2071748 and IL-6 rs1800796 also showed individual associations with male-specific prenatal loss but with homozygous genotypes (homozygosity for the variant allele or the wild-type allele as indicated in Table 3). The odds ratios for these SNPs were between 0.38 and 0.61.

Finally, HLA-E rs1264456 also showed reduced frequency in males for its heterozygosity rate. This association had a borderline statistical significance (P=0.05) and an odds ratio of 0.67. This association represented a deleterious effect of heterozygosity for male offspring, which can be translated into heterozygous advantage for female offspring. All genotypes that showed associations with heterozygosity are discussed below.

The other SNPs listed there did not show any individual association but in combinations they were markers for male-specific prenatal loss. The three SNPs from the HLA complex (HLA-DQA1 rs1142316, HLA-DRA rs7192 and HSPA1B rs1061581) characterize the major HLA complex genetic lineages as first described by Dorak et al. (2006). In the present study, combined homozygosity for ancestral lineages showed a decreased frequency in male newborns compared with the homozygosity rate in female newborns (5.9% in males vs 14.6%, P=0.006, OR=0.36, 95% CI=0.18 to 0.75). The combinations that gave rise to this strong association are homozygosity for wild-type alleles in all three SNPs and homozygosity for variant allele in all three SNPs. Because of its strength, this association remained statistically significant in the multivariable model for prenatal loss as presented below (and in Table 4).

Table 4 lists the nine genotypes identified as independent markers for survival of a male offspring. Seven of those are individual SNP genotypes and two are particular genotype combinations of three SNPs, one in the HLA complex (HLA-DQA1-DRA-HSPA1B) and another in the KLRK1 region. The frequencies in male and female newborns as well as resulting odds ratios and P values are presented.

Likewise, heterozygosity at two IRF4 SNPs rs12203592 and rs872071 did not show an association individually but in combination (i.e., heterozygosity at both SNPs) (10.1% in males vs 19.4% in females, P=0.01, OR=0.47, 95% CI=0.26 to 0.85). This IRF4 combined genotype marker was included in the multivariable model for assessment of its independence but did not remain statistically significant.

Three KLRK1 (NKG2D) region SNPs listed at the end of Table 3 also showed statistically significant or marginally significant associations with odds ratios between 0.60 and 0.69. Since they were from the same gene region (KLRK1), their genotypes were combined to be used as a single marker. The combination included wild-type allele positivity for rs10772266 and heterozygosity for both rs2617160 and rs2617171 (21.7% in males vs 33.3% in females, P=0.01, OR=0.56, 95% CI=0.35 to 0.88). This KLRK1 region combined genotype remained statistically significant as an independent marker in the multivariable model.

Example 11

Multivariable SNP Analysis and Generation of Final Predictive Model

The outcome of pregnancy is not determined by a single genotype and our single marker analysis revealed multiple statistically significant associations. We therefore proceeded to the next step and analyzed the statistically significant associations by multivariable modeling to identify the most informative minimal subset of markers. These would be the statistically most significant and independent associations. Independence is important to avoid redundancy in testing samples and also for contributions to the additive model. Markers that are correlated and therefore not independent do not add to the information obtained from one of them and does not change the odds ratio when included in the multivariable final model.

The multivariable modeling yielded the independence and statistical significance of the nine markers listed in Table 4. The frequencies for each SNP in male and female newborns are replicated from Table 3 and the frequencies for two of the combined genotypes that remained statistically significant in the multivariable model are given in Table 4. In this final model, all but one adjusted odds ratios were smaller than 0.50 and therefore associated with less than 50% likelihood of a male offspring to reach the end of pregnancy.

Next, we assessed the value of this subset of markers in predicting the prenatal loss jointly. Since all associations were arranged to be in the same direction, it was possible to examine the additive effect of the sum of markers without any further manipulation. Each individual was simply given a score for the number of markers possessed. In the newborn group examined, there was no newborn who lacks all of the markers (score=0) or having all of them (score=9). Thus, the scores were between 1 and 8. The newborns were stratified into three groups: the baseline group consisted of newborns possessing any 1 to 3 of the nine markers (n=176), the next group consisted of 141 newborns who possessed any 4 of the nine markers and the third group was 96 newborns positive for any 5 or more of the nine markers.

Examination of the additive effect of these nine SNPs revealed a stepwise decrease in odds ratio corresponding decreasing likelihood of survival for male offspring as the number of markers possessed increases. The overall model reached extreme statistical significance (P<$10^{-10}$). This was because, in reference to the baseline group of newborns possessing 1 to 3 of the markers, having 4 markers was associated with male-specific prenatal loss with an odds ratio of 0.37 (95% CI=0.23 to 0.59; P=0.00001) and again in reference to the baseline group, having 5 or more of the markers was associated with prenatal loss even more strongly (OR=0.20, 95% CI=0.11 to 0.34; P<0.00001). In other words, these figures translate into three-times decreased chance of survival for boys possessing 4 of the nine markers and five-times decreased chance of survival for boys possessing 5 or more compared with boys possessing 3 or fewer markers.

It is important that if such a model is useful in clinical use, the markers should occur at appreciable frequencies in the population. Frequencies of individual markers in newborn males and females are given in Tables 3 and 4. Table 3 shows the results of the analysis of 24 SNPs in newborns. The frequencies for the genotypes shown in male and female newborns, and their statistical evaluation as odds ratio, its 95% confidence interval and P value are shown.

In the cumulative risk model, possession of 4 markers occurred in 38.8% of female newborns, and possession of 5 or more markers in 32.7% of them. It is expected that at the beginning of pregnancy before selection occurs, males have similar frequencies (although at the end of pregnancy, these frequencies are 29.1% and 13.1%, respectively). Thus, at the beginning or at early phases of pregnancy, the risk markers will be present at a considerable frequency in offspring to allow risk stratification.

Experimental Protocols

I. Characterization of Clinical Samples

The population sample analyzed in this study consisted of anonymously collected cord blood samples from newborns in South Wales (United Kingdom). Random, anonymous umbilical cord blood samples were obtained from full-term babies born in the University Hospital of Wales and Llandough Hospital in Cardiff, UK over a period of 12 months from 1996. This practice of collection of surplus biological material for research purposes anonymously was in compliance with the regulations of the local institutional ethics committee.

It was not practically possible to obtain samples from every newborn over this period but no newborn was intentionally excluded on the basis of any selection criteria. The samples were collected until the number in both sex groups exceeded 200. In the final group of 415 newborns, there were 201 boys and 214 girls. This gives a male-to-female (M:F) ratio of 0.939 that is slightly lower than the expected M:F ratio (1.056) in newborns (statistically non-significant).

These samples were previously used to describe the first marker for sex-specific prenatal loss. In the present study, 388 of the originally collected 415 samples were genotyped due to limited DNA availability (201 girls and 187 boys). No data are available about the newborns (such as gestational age, birth order, birth weight, parental age) other than their sex and that they were born via natural vaginal birth. No newborn born via cesarean section was included.

II. Genotyping Procedures

A) Allelic Discrimination Assays

TaqMan allelic discrimination assay utilizes an oligonucleotide probe labeled with a fluorescent reporter dye at the 5' end of the probe and a quencher dye at the 3' end of the probe. The proximity of the quencher to the reporter in the intact probe maintains a reduced fluorescence for the reporter. During the PCR reaction, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

TaqMan allelic discrimination assays were performed on Stratagene MX3000P instruments. The standard thermal profile protocol was used with the modification of 90 seconds at 60° C. for 50 cycles. TaqMan® SNP genotyping assays purchased from ABI as 40× were diluted to 20× by adding Tris-HCl and EDTA at pH 8.0. 96-well plates were set up by adding 1.5 µl DNA (10 ng/µl), 4.625 µl ddH$_2$O and 6.25 µl TaqMan® genotyping master mix (ABI) and 0.625 µl assay reagents. Each plate contained intra and inter-plate controls and no-template controls. Built-in Stratagene Mx3000P software was used to assign genotypes.

B) Polymerase Chain Reaction-Restriction Fragment Length Polymorphism (PCR-RFLP) Analysis In these series of study, PCR-RFLP analysis was performed to genotype the HSPA1B SNP rs1061581. In this analysis, oligonucleotides 5'-CAT CGA CTT CTA CAC GTC CA-3' (SEQ ID NO: 1) and 5'-CAA AGT CCT TGA GTC CCA AC-3' (SEQ ID NO: 2) and the restriction endonuclease PstI were used. In the first step, using the oligonucleotides, a 1,117 bp fragment was amplified by PCR. The fragments were then subjected to restriction endonuclease digestion by using the PstI enzyme. This enzyme cuts the fragment into two fragments of 934 bp and 183 bp when there is a nucleotide G in the SNP position but fails to cut it when there is a nucleotide A in the SNP position. Samples with only 934 bp and 183 bp fragments were classified as homozygote for allele G and samples with only the 1,117 bp fragment were classified as homozygote for allele A. Samples that contained 1,117 bp, 934 bp and 183 bp fragments were classified as heterozygote for alleles A and G.

PCR-RFLP analysis was performed to genotype the HLA-DQA1 3'UTR SNP rs1142316. The symbol "Y" represents the nucleotide sequence characters of T or C. The symbol "R" represents the nucleotide sequence characters of G or A. In this analysis, oligonucleotides 5'-CAA GGG CCA TTG TGA ATC YCC AT-3' (SEQ ID NO: 3) and 5'-TGG GYG GCA RTG CCA A-3'(SEQ ID NO: 4) and the restriction endonuclease BglII were used. The symbol "Y" represents the nucleotide sequence characters of T or C. The symbol "R" represents the nucleotide sequence characters of G or A. In the first step, using the oligonucleotides, a 726 bp fragment was amplified by PCR. PCR was done under standard conditions using 20 ng of genomic DNA and annealing temperature of 57° C. The fragments were then subjected to restriction endonuclease digestion by using the BglII enzyme. This enzyme cuts the fragment into two fragments of 513 bp and 213 bp when there is a nucleotide C in the SNP position but fails to cut it when there is a nucleotide A in the SNP position. Samples with only 513 bp and 213 bp fragments were classified as homozygote for allele C and samples with only the 726 bp fragment were classified as homozygote for allele A. Samples that contained 726 bp, 513 bp and 213 bp fragments were classified as heterozygote for alleles A and C.

PCR-RFLP analysis was also used to genotype MDM2 SNP rs2279744. For the MspA1I RFLP analysis, primers 5'-CGG GAG TTC AGG GTA AAG GT-3' (SEQ ID NO: 5) and oligonucleotide 5'-AGC AAG TCG GTG CTT ACC TG-3' (SEQ ID NO: 6) were used. PCR was done under standard conditions using 20 ng of genomic DNA and annealing temperature of 66° C. The resulting PCR product (351 bp) was digested by MspA1I. MspA1I cleaves final PCR product on two sites, one is constitutive that served as an internal control of enzymatic digestion and allele G of SNP309 generates specific MspA1I restriction site.

Table 5 shows the flanking DNA sequence of each SNP. The SNPs are shown as the wild-type and variant alleles.

Table 6 lists the different genotyping methods used to genotype SNPs analyzed in this invention.

III. Statistical Analysis

The statistical analysis of a SNP association may be performed using the following statistical models. It may be of importance to have the variant allele in homozygous or heterozygous combination as long as there is at least one copy of it in the genotype (CT and TT). In this case, individuals with CT or TT genotypes are pooled together and coded as 1 in a variable that are going to be used in the statistical analysis. The code 1 indicates presence of the susceptibility marker. In this case, individuals who have the homozygous wild-type genotype are coded as 0 meaning the lack of the susceptibility marker. This model that pools heterozygotes and homozygotes together is called dominant genetic model.

In recessive model, the interest in on homozygous genotype of the variant allele (TT) and individuals with the TT genotype are coded as 1 while all other genotypes are coded as 0. There are certain situations in which the number of variant allele possessed is important because having 1 or 2 copies of the variant allele correlates with the degree of susceptibility. In this case, individuals with genotype CT (one copy of the variant allele) have increased susceptibility and individuals with genotype TT (two copies of the variant allele) have an even higher degree of susceptibility. This model is called the additive model and demonstrates a gene-dosage effect. In most cases, statistical significance for this model is usually an indication of an association with dominant or recessive model. In our analysis that follows, we have presented dominant or recessive model associations for each SNP. Variables with P values of less than 0.05 were considered statistically significant. Statistical association analysis was carried out using logistic regression with Stata version 10 statistical software.

One exceptional situation is that the heterozygous genotype CT may be of importance. Heterozygosity in the genome is shown to be a beneficial trait for prevention from many common diseases including infections and cancer. This situation is called 'heterozygote advantage' and is characterized by decreased frequency or underrepresentation of a heterozygous genotype among cases with a disease compared with normal controls because of its protective effect from the condition. In prenatal selection, heterozygote advantage confers survival benefit is observed at higher frequency. The dependency of the HLA complex-mediated heterozygote advantage on sex in prenatal selection has already been reported.

As mentioned above, each individual is coded as 0 or 1 based on the absence or presence of the susceptibility genotype(s) for each SNP before statistical association. A SNP may have a deleterious or beneficial effect on a condition. In the present invention, the outcome of interest was sex-specific prenatal survival. In this case, beneficial genotypes are overrepresented in the favored sex and deleterious genotypes for a particular sex are underrepresented in that sex group among newborns who have survived the selection. To avoid intricate mathematical manipulations while constructing a statistical model to find the most informative subset of SNPs, it is desirable that all SNPs are beneficial or deleterious. This means, it is easier to construct a model if the direction of the effect is the same for each SNP. In the case of SNP associations, this is achieved easily. Since each individual is coded as 0 or 1, when necessary, an association that is beneficial for one sex can be converted to a deleterious one by simply reversing the statistical codes. Males are under greater selective pressure during pregnancy and our aim was to find deleterious genotypes for males. We were interested in genotypes that were underrepresented in male newborns compared with female newborns. All results presented here are in this direction and the genotypes that give rise to an association in that direction (i.e., deleterious for males) are given in the text and tables. In terms of the odds ratio, which is a measure of the strength of association, they are all less than 1.0. The odds ratio approximates the survival chance of a male fetus to the end of pregnancy. Thus, a value of 0.49 suggests, a male conceptus with this genotype has a survival probability of 49% as opposed to 100% for the comparison group who are female newborns.

All patents, publications, accession numbers, and patent application described supra in the present application are hereby incorporated by reference in their entirety.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Bergeron R J. Iron: A controlling nutrient in proliferative processes. Trends Biochem Sci 1986; 11(133):133-136.
2. Boklage C E. Survival probability of human conceptions from fertilization to term. Int J Fertil 1990; 35(2):75, 79-80, 81-94.
3. Bombell S, McGuire W. Cytokine polymorphisms in women with recurrent pregnancy loss: meta-analysis. Aust NZ J Obstet Gynaecol 2008; 48(2):147-54.
4. Campbell H, Carothers A D, Rudan I et al. Effects of genome-wide heterozygosity on a range of biomedically relevant human quantitative traits. Hum Mol Genet 2007; 16:233-41.
5. Carrington M, Nelson G W, Martin M P, Kissner T, Vlahov D, Goedert J J, Kaslow R, Buchbinder S, Hoots K, O'Brien S J. HLA and HIV-1: heterozygote advantage and B*35-Cw*04 disadvantage. Science 1999; 283(5408):1748-52.
6. Christiansen O B, Nielsen H S, Kolte A, Pedersen A T. Research methodology and epidemiology of relevance in recurrent pregnancy loss. Semin Reprod Med 2006; 24(1):5-16.
7. Denic S, Nagelkerke N, Nicholls M G. Germline genomic homozygosity and cancer risk. JAMA 2008; 300(2):169-70.
8. Denschlag D, Marculescu R, Unfried G, Hefler L A, Exner M, Hashemi A, et al. The size of a microsatellite polymorphism of the heme oxygenase 1 gene is associated with idiopathic recurrent miscarriage. Mol Hum Reprod 2004; 10(3):211-4.
9. Dorak M T, Lawson T, Machulla H K, Mills K I, Burnett A K. Increased heterozygosity for MHC class II lineages in newborn males. Genes Immun 2002; 3:263-9.
10. Dorak M T, Shao W, Machulla H K G, Lobashevsky E S, Tang J, Park M H, Kaslow, R A. Conserved extended haplotypes of the MHC. Genes Immun 2006; 7:450-67.
11. Drife J O. What proportion of pregnancies are spontaneously aborted? British Medical Journal 1983; 286:294.
12. Goodman C, Jeyendran R S, Coulam C B. P53 tumor suppressor factor, plasminogen activator inhibitor, and vascular endothelial growth factor gene polymorphisms and recurrent implantation failure. Fertil Steril 2009 (in press).
13. Hanna J, Goldman-Wohl D, Hamani Y et al. Decidual NK cells regulate key developmental processes at the human fetal-maternal interface. Nat Med 2006; 12:1065-74.

14. Hayashi T et al. Identification of the NKG2D haplotypes associated with natural cytotoxic activity of peripheral blood lymphocytes and cancer immunosurveillance. Cancer Res 2006; 66:563-70.
15. Healey C S, Dunning A M, Teare M D, Chase D, Parker L, Burn J, Chang-Claude J, Mannermaa A, Kataja V, Huntsman D G, Pharoah P D, Luben R N, Easton D F, Ponder B A. A common variant in BRCA2 is associated with both breast cancer risk and prenatal viability. Nat Genet 2000; 26(3):362-4.
16. Hu W, Feng Z, Teresky A K, Levine A J. p53 regulates maternal reproduction through LIF. Nature 2007; 450(7170):721-4.
17. Kantarci O H, Hebrink D D, Schaefer-Klein J, Sun Y, Achenbach S, Atkinson E J, Heggarty S, Cotleur A C, de Andrade M, Vandenbroeck K, Pelfrey C M, Weinshenker B G. Interferon gamma allelic variants: sex-biased multiple sclerosis susceptibility and gene expression. Arch Neurol 2008; 65(3):349-57.
18. Kostyu D D. HLA: fertile territory for developmental genes? Crit Rev Immunol 1994; 14(1):29-59.
19. Lerner S P, Finch C E. The major histocompatibility complex and reproductive functions. Endocr Rev 1991; 12(1):78-90.
20. Mastenbroek S, Twisk M, van Echten-Arends J, Sikkema-Raddatz B, Korevaar J C, Verhoeve H R, Vogel N E, Arts E G, de Vries J W, Bossuyt P M, Buys C H, Heineman N U, Repping S, van der Veen F. In vitro fertilization with preimplantation genetic screening. N Engl J Med 2007; 357(1):9-17.
21. McMillen M M. Differential mortality by sex in fetal and neonatal deaths. Science 1979; 204(4388):89-91.
22. Mincheva-Nilsson L, Nagaeva O, Chen T, Stendahl U, Antsiferova J, Mogren I, Hernestål J, Baranov V. Placenta-derived soluble MHC class I chain-related molecules down-regulate NKG2D receptor on peripheral blood mononuclear cells during human pregnancy: a possible novel immune escape mechanism for fetal survival. J Immunol 2006; 176(6):3585-92.
23. Ober C, Elias S, Kostyu D D, Hauck W W. Decreased fecundability in Hutterite couples sharing HLA-DR. Am J Hum Genet 1992; 50(1):6-14.
24. Pietrowski D, Bettendorf H, Riener E K, Keck C, Hefler L A, Huber J C, et al. Recurrent pregnancy failure is associated with a polymorphism in the p53 tumor suppressor gene. Hum Reprod 2005; 20(4):848-51.
25. Raulet D H. Roles of the NKG2D immunoreceptor and its ligands. Nat Rev Immunol 2003; 3(10):781-90.
26. Roberts C J & Lowe C R. Where have all the conceptions gone? Lancet 1975; 1:498-499.
27. Sargent I L, Borzychowski A M, Redman C W. NK cells and human pregnancy-an inflammatory view. Trends Immunol 2006; 27(9):399-404
28. Sierra S, Stephenson M. Genetics of recurrent pregnancy loss. Semin Reprod Med 2006; 24(1):17-24.
29. Steck T, Giess R, Suetterlin M W, Bolland M, Wiest S, Poehls U G, Dietl J. Leukemia inhibitory factor (LIF) gene mutations in women with unexplained infertility and recurrent failure of implantation after IVF and embryo transfer. Eur J Obstet Gynecol Reprod Biol 2004; 112(1):69-73.
30. Ucisik-Akkaya E, Dorak M T. A study of natural killer cell lectin-like receptor K1 gene (KLRK1/NKG2D) region polymorphisms in a European population sample. Tissue Antigens 2009; 73(2): 177-83.
31. Vatten L J, Skjaerven R. Offspring sex and pregnancy outcome by length of gestation. Early Hum Dev 2004; 76(1):47-54.
32. That W, Nielsen R, Slatkin M. An investigation of the statistical power of neutrality tests based on comparative and population genetic data. Mol Biol Evol 2009; 26(2): 273-83.
33. Ziegler A, Kentenich H, Uchanska-Ziegler B. Female choice and the MHC. Trends Immunol 2005; 26(9):496-502.

TABLE 1

List of Genes and SNP Evaluated for Their Predictive Value as Markers for Prenatal Loss

| Genes and SNP Position | SNP ID | Chromosome position |
|---|---|---|
| HFE2 (HJV)-5'FLANK | rs4970862 | chr1:144132834 |
| HFE2 (HJV)-3'FLANK | rs16827043 | chr1:144106797 |
| IL10 | rs1800896 | chr1:205013520 |
| PKR (EIF2AK2) - IVS2 | rs2270414 | chr2:37216952 |
| PKR (EIF2AK2) - IVS1 | rs12712526 | chr2:37224339 |
| PKR (EIF2AK2) - 5'UTR | rs2254958 | chr2:37229795 |
| RRM2-5'UTR | rs1130609 | chr2:10180371 |
| STEAP3-5'UTR | rs1562256 | chr2:119687643 |
| STEAP3-ivs1 | rs865688 | chr2:119699720 |
| STEAP3-IVS1 | rs865108 | Chr2:119702854 |
| CYBRD1-IVS1 | rs960748 | chr2:172088182 |
| CYBRD1-IVS1 | rs6759240 | chr2:172089044 |
| CYBRD1-ex4 (G266A) | rs10455 | chr2:172119519 |
| SLC40A1(V221V) | rs2304704 | chr2:190138422 |
| SLC40A1 - IVS2 | rs1439812 | chr2:190148793 |
| SLC40A1 - IVS2 | rs1439814 | chr2:190151138 |
| SLC40A1 - IVS7 | rs1439816 | chr2:190152875 |
| SLC11A1/NRAMP1-IVS4 | rs3731865 | chr2:218958247 |
| SLC11A1/NRAMP1-5'UTR | rs1059823 | chr2:218968088 |
| TF-P589S (Ex 15) | rs1049296 | chr3:134977044 |
| TF-L524L (Ex 13) | rs8649 | chr3:134969648 |
| TF-5' UTR | rs1130459 | chr3:134947973 |
| TF-5' FLANK | rs4481157 | chr3:134947374 |
| TF-5' FLANK | rs16840812 | chr3:134945497 |
| CP-E543D (Ex 9) | rs701753 | chr3:150398925 |
| CP-IVS1 | rs7652826 | chr3:150421640 |
| TFRC-S142G (Ex 4) | rs3817672 | chr3:197285208 |
| TFRC (5'UTR) | rs11915082 | chr3:197293536 |
| NFKB1-IVS6 | rs4648022 | chr4:103715475 |
| DAXX-IVS1 | rs2073524 | chr6:33398525 |
| DAXX-Y379Y (ex4) | rs1059231 | 33396249 |
| DAXX-IVS4 | rs2239839 | 33396053 |
| RXRB-5'FLANK | rs421446 | 33282761 |
| RXRB-5'FLANK | rs365339 | 33280883 |
| RXRB-IVS3 | rs2076310 | 33274012 |
| RXRB-F384F | rs6531 | 33271429 |
| BRD2-3'UTR | rs1049414 | 33056585 |
| BRD2-IVS7 | rs11908 | 33052724 |
| BRD2-IVS3 | rs635688 | 33051129 |
| BRD2-5'FLANK | rs206786 | 33043157 |
| TAP2 | rs241453 | 32904204 |
| HLA-DQB2 | rs1573649 | 32839236 |
| HLA-DQA2 | rs2227128 | 32819378 |
| HLA-DQA1-3'UTR | rs1142316 | 32686523 |
| HLA-DQA1-IVS2 | rs9272723 | 32717405 |
| HLA-DQA1-IVS1 | rs17426593 | 32716055 |
| HLA-DRB1 to DQA1 | rs17599077 | 32699036 |
| HLA-DRB1 to DQA1 | rs3129763 | 32698903 |
| HLA-DRB1 to DQA1 | rs9271586 | 32698877 |
| HLA-DRB1 to DQA1 | rs2395225 | 32698602 |
| HLA-DRB1 to DQA1 | rs3135005 | 32693997 |
| DRA-3'FLANK | rs3135388 | 32521029 |
| DRA-3'UTR | rs7194 | 32520458 |
| DRA-L242V (exon 4) | rs7192 | 32519624 |
| DRA-I134I (exon 3) | rs8084 | 32519013 |
| DRA-V16L (exon 1) | rs16822586 | 32515751 |
| DRA-5'UTR | rs14004 | 32515687 |
| BTNL2 (Q350Q) | rs9268480 | 32471822 |
| BTNL2 | rs2076530 | chr6:32471794 |
| BTNL2 | rs3129953 | 32469799 |
| C6orf10 | rs9268428 | 32452951 |
| C6orf10-IVS6 | rs1265758 | 32431507 |
| NOTCH4-5'FLANK | rs3096690 | 32302608 |
| NOTCH4-5'FLANK | rs3096702 | 32300309 |
| NOTCH1-IVS1 | rs396960 | 32299559 |

TABLE 1-continued

List of Genes and SNP Evaluated for Their
Predictive Value as Markers for Prenatal Loss

| Genes and SNP Position | SNP ID | Chromosome position |
|---|---|---|
| NOTCH4-K117Q (exon 3) | rs915894 | 32298368 |
| NOTCH4-S244L (exon 4) | rs8192585 | 32296801 |
| NOTCH4-IVS11 | rs3134799 | 32292199 |
| PBX2-IVS4 | rs204993 | 32263559 |
| PBX2-3'FLANK | rs1800684 | 32259972 |
| EGFL8-3'UTR | rs1061808 | 32244525 |
| EGFL8-R86K | rs3096697 | 32242488 |
| TNXB-3'UTR | rs8283 | 32191278 |
| TNXB-3'FLANK | rs3130342 | 32188124 |
| TNXB-H1248R | rs185819 | 32158045 |
| CYP21A2-V282L | rs6471 | 32115866 |
| CYP21A2-R103K | rs6474 | 32114865 |
| SKIV2L-Y1067Y (exon 26) | rs410851 | 32044647 |
| SKIV2L-IVS6 | rs419788 | 32036778 |
| SKIV2L-IVS6 | rs2280774 | 32036670 |
| SKIV2L Ex5 Q151R | rs438999 | 32036285 |
| SKIV2L-IVS2 | rs440454 | 32035321 |
| CFB-IVS14 | rs1270942 | 32026839 |
| CBF-R32W | rs12614 | 32022158 |
| HSPA1B-Q351Q | rs1061581 | 31904709 |
| HSPA1B-5'FLANK (−1136) | rs2763979 | 31902571 |
| HSPA1A-5'UTR (−27G > C) | rs1043618 | 31891486 |
| HSPA1L-T493M | rs2227956 | chr6:31886251 |
| HSPA1L-G602K | rs2075800 | 31885925 |
| MSH5 | rs1802127 | 31837904 |
| MSH5-Q716Q | rs707938 | 31837338 |
| MSH5 | rs3131378 | 31833264 |
| MSH5 | rs707939 | 31834667 |
| MSH5 | rs28381349 | 31817024 |
| MSH5 | rs2075789 | 31816307 |
| CLIC1 | rs3131383 | 31812273 |
| CLIC1 | rs2272592 | 31806331 |
| BAT3-IVS6 | rs805303 | 31724345 |
| BAT3-IVS12 | rs2077102 | 31719819 |
| BAT3-3'FLANK | rs2736155 | 31713178 |
| AIF1-IVS4/R15W | rs2269475 | 31691910 |
| AIF1-5'UTR/IVS3 | rs2259571 | 31691806 |
| AIF1-IVS1 | rs2844475 | 31691134 |
| NCR3-5'UTR | rs986475 | 31664688 |
| NCR3-3'UTR | rs1052248 | 31664560 |
| NCR3-3'FLANK | rs2256965 | 31663109 |
| TNF (promoter −238) | rs361525 | 31651080 |
| TNF-5'FLANK (promoter −857) | rs1799724 | 31650461 |
| LTA-IVS1 | rs909253 | 31648292 |
| NFKBIL1 | rs2071592 | 31623319 |
| MICA-V152M | rs1051792 | 31486956 |
| HLA-C-5'FLANK | rs9264942 | 31382359 |
| POU5F1-IVS1 (Ex1-M1R) | rs3130932 | 31241922 |
| POU5F1-IVS4 | rs2394882 | 31240628 |
| TCF19-P219P | rs2073722 | 31237621 |
| TCF19-IVS1 | rs6905862 | 31235581 |
| TCF19-IVS1 | rs1150765 | chr6:31235541 |
| GTF2H4-IVS11 | rs1264307 | 30988736 |
| GTF2H4 | rs1264309 | 30983878 |
| GTF2H4-5'FLANK | rs3909130 | 30982144 |
| DDR1 | rs1049623 | 30972808 |
| DDR1 | rs1264323 | 30963886 |
| DDR1 | rs1264327 | 30958561 |
| DDR1 | rs1264328 | 30958121 |
| IER3-3'UTR | rs10947089 | 30818114 |
| HLA-E - 3'FLANK | rs1264456 | 30570063 |
| HLA-E - 5'FLANK | rs1264459 | 30563899 |
| ZNRD1 | rs9261269 | 30138093 |
| HLA-G - 3'UTR | rs1704 | 29906560 |
| HLA-G - 5'FLANK | rs1736939 | 29901364 |
| UBD (5'FLANK) | rs1233405 | 29637733 |
| UBD (IVS1) | rs2534790 | 29632147 |
| UBD (Ex2-T68C) | rs2076485 | 29631931 |
| UBD (Ex2-C160S) | rs8337 | 29631655 |
| HIST1H1T-V14L | rs198844 | 26216261 |
| HIST1H4C-5'FLANK | rs198853 | 26212075 |
| HIST1H4C-5' & HFE-3'FLANK | rs17596719 | 26205173 |
| HIST1H4C-5' & HFE-3'FLANK | rs12346 | 26205025 |
| HFE-3'FLANK | rs707889 | 26203910 |
| HFE-IVS5 | rs2858996 | 26202005 |
| HFE-C282Y | rs1800562 | 26201120 |
| HFE-H63D | rs1799945 | 26199158 |
| HFE-S65C | rs1800730 | 26199164 |
| HFE-IVS2 | rs2071303 | 26199315 |
| HFE-IVS1 | rs9366637 | 26197077 |
| HFE-5'FLANK | rs2794719 | chr6:26196869 |
| HFE-5'FLANK | rs2794720 | 26195181 |
| HFE-5'FLANK | rs1800702 | 26194442 |
| HFE-5'FLANK | rs4529296 | 26191114 |
| HFE-HIST1H1C intergenic | rs2050947 | 26178058 |
| HIST1H1C-5'FLANK | rs807212 | 26173600 |
| HIST1H1C-5'FLANK | rs9358903 | 26169928 |
| HIST1H1C 5'FLANK | rs9393682 | 26165029 |
| HIST1H1C-S36S | rs10425 | 26164528 |
| HIST1H1C-P195P | rs8384 | 26164051 |
| HIST11H2AB-L97L | rs2230655 | 26141485 |
| HIST1H3B (3'UTR) | rs2213284 | 26139847 |
| HIST1H4A (5'FLANK) | rs9467664 | 26129792 |
| SLC17A3 | rs1165165 | 25970445 |
| PRL (promoter) | rs1341239 | 22412183 |
| CDKAL1 | rs6908425 | 20836710 |
| Ch6:20099022 | rs965036 | 20099022 |
| EDN1-3'FLANK | rs4714384 | 12405839 |
| EDN1-3'FLANK | rs4714383 | 12405468 |
| EDN1 (K198N - Ex5) | rs5370 | 12404241 |
| EDN1-IVS4 | rs1626492 | 12403489 |
| EDN1-IVS2 | rs1476046 | 12401207 |
| EDN1-5'FLANK | rs3756863 | 12397016 |
| Ch6:9559183 | rs10484246 | 9559183 |
| IRF4 | rs4985288 | 327246 |
| IRF4 | rs9405192 | 327537 |
| IRF4-5'FLANK | rs1033180 | 328546 |
| IRF4-IVS4 | rs12203592 | 341321 |
| IRF4 | rs3778607 | 348799 |
| IRF4 | rs2001508 | chr6:349632 |
| IRF4 | rs7768807 | 353246 |
| IRF4 | rs1877175 | 355493 |
| IRF4-3'UTR | rs9392502 | 355608 |
| IRF4-3'UTR | rs872071 | 356064 |
| IRF4 | rs11242865 | 356954 |
| IRF4 | rs7757906 | 357741 |
| IRF4 | rs9378805 | 362727 |
| IGFBP3-5' FLANK | rs2854744 | chr7:45927600 |
| TFR2-IVS17 | rs10247962 | chr7:100057865 |
| TFR2-IVS3 | rs7385804 | chr7:10073906 |
| TFR2-5' FLANK | rs4434553 | chr7:10078127 |
| SLC39A14-5' FLANK | rs4872476 | chr8:22266179 |
| SLC39A14-5' FLANK | rs11136002 | chr8:22273027 |
| SLC39A14-L33C | rs896378 | Chr8:22318266 |
| SLC39A14-IVS8 | rs10101909 | chr8:22332985 |
| H19 | rs217727 | chr11:1973484 |
| RRM1-IVS2 | rs232054 | chr11:4080003 |
| KLRK1 3' | rs10772266 | chr12:10397436 |
| KLRK1 3' | rs1049174 | chr12:10416632 |
| KLRK1 (intron 1) | rs2617160 | chr12:10436864 |
| KLRK1 (intron 1) | rs2246809 | chr12:10448311 |
| KLRC4 (intron 3) | rs2734565 | chr12:10451858 |
| KLRC4 S104N (ex3) | rs2617170 | chr12:10452224 |
| KLRC4 (intron 2) | rs2617171 | chr12:10452546 |
| KLRC4 S29I (ex1) | rs1841958 | chr12:10453356 |
| KLRC1-5'FLANK | rs1983526 | chr12:10499280 |
| KLRC1-5'FLANK | rs2900421 | chr12:10513314 |
| SLC11A2 (NRAMP2)- IVS4 | rs224589 | chr12:49685317 |
| SLC11A2 (NRAMP2)- IVS1 | rs422982 | chr12:49692621 |
| SLC11A2 (NRAMP2)- IVS1 | rs224575 | chr12:49705888 |
| IFNG-3' FLANK | rs2069727 | chr12:66834490 |
| MDM2-IVS1 (SNP309) | rs2279744 | chr12:67488847 |
| IGF1 Exon 4 - 3' UTR | rs6220 | chr12:101318645 |
| IGF1 - IVS3 | rs1520220 | chr12:101320652 |
| IREB2 | rs2656070 | chr15:76517307 |
| IGF1R - Exon 16 - E1043E | rs2229765 | chr15:97295748 |
| HP_5'UTR | rs9924964 | chr16:70643062 |
| HP_5'UTR | rs7203426 | Chr16:70644056 |
| HP_IVS1 | rs2070937 | chr16:70647241 |
| TP53_Ex4 R72P | rs1042522 | chr17:7520197 |

TABLE 1-continued

List of Genes and SNP Evaluated for Their Predictive Value as Markers for Prenatal Loss

| Genes and SNP Position | SNP ID | Chromosome position |
|---|---|---|
| BRIP1-IVS4 | rs4968451 | chr17:57282089 |
| HAMP-5'FLANK | rs1882694 | chr19:40463222 |
| HAMP-5'FLANK | rs10414846 | chr19:40464311 |
| HAMP-IVS1 | rs8101606 | ch19:40466396 |
| HAMP-IVS1 | rs7251432 | chr19:40467281 |
| BMP2-3'FLANK | rs235756 | chr20:6715111 |
| LIF-3'UTR | rs929271 | chr22:28968226 |
| LIF-IVS2 | rs737921 | chr22:28970214 |
| LIF-IVS2 | rs929273 | chr22:28970595 |
| LIF-5'FLANK | rs2267153 | chr22:28973609 |
| LIF-5'FLANK | rs3761427 | chr22:28974826 |
| LIF-5'FLANK | rs9606708 | chr22:28976126 |
| HMOX1 - IVS1 | rs2071748 | chr22:34107618 |
| HMOX1 - IVS2 | rs9607267 | chr22:34111207 |
| HMOX1 - IVS3 | rs2071749 | chr22:34113413 |
| HMOX1-3'UTR | rs743811 | chr22:34122974 |
| TMPRSS6-Y739Y | rs2235321 | chr22:35792872 |
| TMPRSS6-V736A (Ex17) | rs855791 | chr22:35792882 |
| TMPRSS6-D511D (Ex13) | rs4820268 | chr22:35799537 |
| TMPRSS6-IVS2 | rs733655 | chr22:35824997 |
| TMPRSS6-5'UTR | rs5756515 | chr22:35829638 |
| HEPH-5'FLANK | rs5919015 | X chr:65299410 |
| HEPH-5'UTR | rs1028348 | X chr:65300888 |
| HEPH-IVS7 | rs760866 | X chr:65330706 |
| HEPH-Exon 13 (Y498Y) | rs806607 | X chr:65343765 |
| HEPH-Exon 13 (T526T) | rs809363 | X chr:65343849 |
| HEPH-IVS14 | rs708966 | X chr:65370647 |
| HEPH-IVS18 | rs4827365 | X chr:65397067 |
| HEPH-IVS18 | rs2198868 | X chr:65399577 |

TABLE 2

Characteristics of Single Nucleotide Polymorphisms and Other Polymorphisms Found To Be Predictors of Prenatal Loss in Univariable Statistical Association Tests

| Genes | SNP name | Alternative Name | Position in Gene/Change |
|---|---|---|---|
| RXRB | rs421446 | NT_007592.14:g.24033033A > G | 5' flanking region, T > C |
| RXRB | rs2076310 | NT_007592.14:g.24024284A > G | intron 3, T > C |
| BRD2 | rs635688 | NT_007592.14:g.23801401T > C | intron 3, C > T |
| HLA-DQA1 | rs1142316 | no alternative name | 3'UTR, A > C |
| HLA-DRA | rs7192 | NT_007592.14:g.23269895T > G | exon 4, G > T (L242V) |
| HSPA1B | rs1061581 | no alternative name | exon 1, A > G (Q351Q) |
| GTF2H4 | rs3909130 | NT_007592.14:g.21732416A > G | 5' flanking region, C > T |
| HLA-E | rs1264456 | no alternative name | 3' flanking region, C > T |
| HIST1H1T | rs198844 | NT_007592.14:g.16966532C > G | exon 1, C > G (L14V) |
| IRF4 | rs12203592 | NT_034880.3:g.336321C > T | intron 4, C > T |
| IRF4 | rs872071 | NT_034880.3:g.351064A > G | 3'UTR, G > A |
| LIF | rs929271 | NT_011520.11:g.10028795T > G | 3'UTR, T > G |
| TP53 | rs1042522 | NT_010718.15:g.7176820G > C | exon 4, C > G (R72P) |
| MDM2 | rs2279744 | NT_029419.11:g.31345886T > G | intron 1, T > G (SNP309) |
| SLC11A2 (NRAMP2) | rs422982 | NT_029419.11:g.13549660T > A | intron 1, T > A |
| SLC40A1 | rs1439814 | NT_005403.16:g.40652310C > T | intron 2, T > C |
| RRM2 | rs1130609 | NT_005334.15:g.5097055T > G | 5'UTR, G > T |
| TMPRSS6 | rs733655 | NT_011520.11:g.16885566T > C | intron 2, T > C |
| HMOX1 | rs2071748 | NT_011520.11:g.15168187G > A | intron 1, G > A |
| IFNG | rs2069727 | NT_029419.11:g.30691529T > C | 3' flanking region, A > G |
| IL6 | rs1800796 | NT_007819.16:g.22255204G > C | promoter, G > C |
| KLRK1 region | rs10772266 | no alternative name | intergenic |
| KLRK1 region | rs2617160 | NT_009714.16:g.3304571A > T | intron 1, A > T |
| KLRK1 region | rs2617171 | NT_009714.16:g.3320253C > G | intron 2, C > G |

TABLE 3

Individual Predictive Value of the Single Nucleotide Polymorphisms and Other Polymorphisms or Their Combinations

| Genes/SNP/Genotypes | Frequency in Males vs Females (%) | Univariable Odds Ratio (95% CI) and P value |
|---|---|---|
| RXRB rs421446/ variant allele positivity | 45.2 vs 55.3 | OR = 0.66 (0.44 to 0.99), P = 0.05 |
| RXRB rs2076310/ variant allele positivity | 35.7 vs 49.0 | OR = 0.58 (0.38 to 0.87), P = 0.009 |
| BRD2 rs635688/ wildtype allele positivity | 71.5 vs 80.2 | OR = 0.62 (0.38 to 0.99), P = 0.05 |
| HLA-DQA1 rs1142316 */ combined homozygous genotypes | 58.7 vs 59.1 | OR = 0.99 (0.64 to 1.50), P = 0.94 |
| HLA-DRA rs7192 */combined homozygous genotypes | 52.4 vs 58.7 | OR = 0.78 (0.52 to 1.16), P = 0.22 |
| HSPA1B rs1061581 */ combined homozygous genotypes | 50.0 vs 54.0 | OR = 1.17 (0.80 to 1.73), P = 0.42 |
| GTF2H4 rs3909130/ wildtype allele positivity | 89.0 vs 95.7 | OR = 0.37 (0.16 to 0.82), P = 0.02 |
| HLA-E rs1264456/ heterozygosity | 37.6 vs 47.3 | OR = 0.67 (0.45 to 1.00), P = 0.05 |
| HIST1H1T rs198844/ variant allele positivity | 18.1 vs 28.9 | OR = 0.54 (0.33 to 0.89), P = 0.02 |
| IRF4 rs12203592/ heterozygosity | 35.7 vs 32.7 | OR = 0.73 (0.48 to 1.13), P = 0.16 |
| IRF4 rs872071/ heterozygosity | 45.5 vs 52.9 | OR = 0.74 (0.49 to 1.12), P = 0.16 |
| LIF rs929271 **/ wild-type homozygosity | 42.4 vs 51.0 | OR = 0.71 (0.47 to 1.07), P = 0.10 |
| TP53 rs1042522 **/ wild-type homozygosity | 55.0 vs 58.0 | OR = 0.88 (0.59 to 1.31), P = 0.54 |

TABLE 3-continued

Individual Predictive Value of the Single Nucleotide Polymorphisms and Other Polymorphisms or Their Combinations

| Genes/SNP/Genotypes | Frequency in Males vs Females (%) | Univariable Odds Ratio (95% CI) and P value |
|---|---|---|
| MDM2 rs2279744 **/ wild-type homozygosity | 45.2 vs 45.2 | OR = 1.00 (0.67 to 1.47), P = 0.99 |
| SLC11A2 rs422982/ variant allele positivity | 40.3 vs 50.2 | OR = 0.67 (0.45 to 1.0), P = 0.05 |
| SLC40A1 rs1439814/ variant allele positivity | 57.4 vs 67.5 | OR = 0.65 (0.43 to 0.98), P = 0.04 |
| RRM2 rs1130609/ variant allele positivity | 38.2 vs 48.1 | OR = 0.66 (0.44 to 1.01), P = 0.06 |
| TMPRSS6 rs733655/ variant allele homozygosity | 2.03 vs 5.16 | OR = 0.38 (0.12 to 1.22), P = 0.10 |
| HMOX1/rs2071748/ variant allele homozygosity | 14.7 vs 22.1 | OR = 0.61 (0.36 to 1.02), P = 0.06 |
| IFNG rs2069727/ wild-type allele positivity | 80.1 vs 87.7 | OR = 0.56 (0.33 to 0.97), P = 0.04 |
| IL6 rs1800796/ wildtype homozygosity | 81.4 vs 88.0 | OR = 0.60 (0.34 to 1.04), P = 0.07 |
| KLRK1 rs10772266 ***/ wild-type allele positivity | 70.9 vs 80.1 | OR = 0.60 (0.38 to 0.97), P = 0.04 |
| KLRK1 rs2617160 ***/ heterozygosity | 34.8 vs 43.6 | OR = 0.69 (0.46 to 1.05), P = 0.08 |
| KLRK1 rs2617171 ***/ heterozygosity | 35.9 vs 44.6 | OR = 0.69 (0.46 to 1.05), P = 0.08 |

\* These SNPs make up the HLA-DQA1-DRA-HSPA1B haplotype. Individually they have no effect on prenatal loss.
\*\* These SNPs do not show any effect on prenatal loss but in interaction with MDM2 and TP53 SNPs, the LIF SNP influences viability of male offspring.
\*\*\* Individually, these SNPs do not show any effect individually but in combination of the genotypes shown, they are a combined KLRK1 marker for loss of male offspring before birth.

TABLE 4

Single nucleotide polymorphisms and other polymorphisms found to be independent predictors of prenatal loss in multivariable statistical modeling

| Gene/SNP/Genotype | Frequency in Males vs Females (%) | Adjusted odds ratio (95% CI) and P value |
|---|---|---|
| RXRB rs2076310/ variant allele positive | 35.7 vs 49.0 | OR = 0.45 (0.27 to 0.74), P = 0.002 |
| HLA-DQA1 rs1142316/ homozygosity | 5.85 vs 14.6 | OR = 0.31 (0.13 to 0.77), P = 0.01 |
| HLA-DRA rs7192/ homozygosity | | |
| HSPA1B rs1061581/ homozygosity | | |
| GTF2H4 rs3909130/ wildtype allele positive | 89.0 vs 95.7 | OR = 0.28 (0.09 to 0.81), P = 0.02 |
| HIST1H1T rs198844/ variant allele positive | 18.1 vs 28.9 | OR = 0.47 (0.26 to 0.85), P = 0.01 |
| IFNG rs2069727/ wildtype allele positive | 80.1 vs 87.7 | OR = 0.47 (0.24 to 0.91), P = 0.03 |
| IL6 rs1800796/ wildtype homozygous | 81.4 vs 88.0 | OR = 0.38 (0.19 to 0.78), P = 0.008 |
| KLRK1 rs10772266/ wildtype allele positive | 21.7 vs 33.3 | OR = 0.55 (0.32 to 0.96), P = 0.035 |
| KLRK1 rs2617160/ heterozygous | | |
| KLRK1 rs2617171/ heterozygous | | |
| TMPRSS6 rs733655/ variant homozygous | 2.03 vs 5.16 | OR = 0.09 (0.01 to 0.78), P = 0.03 |
| HMOX1 rs2071748/ variant homozygous | 14.7 vs 22.1 | OR = 0.47 (0.24 to 0.90), P = 0.02 |

TABLE 5

Single Nucleotide Polymorphisms Found to Predict Sex-Specific Prenatal Selection

```
RXRB rs421446 C/T:
GAGGGCCACC TGTTCCAAGA CCCCCTTTCA AGGCCAGACT
GGACACCAAG ATGGGGCCAT GAACAAATCA CCCTTGGGGA
CCATAAGAAC CCAGGGAGTT GGGGGGAGGG GACTGGTGCT
GCAGAACCAG TGGAAAGGGG TGACGCACGA ACCCCTCCCT
C/T
CAAAAAGACC CGGAGTGTCA CGCATACACA GTGACACATA
CTCTTTCCTC TCACACCCGG CGGCGGGGGT TGCCCTGGGA
GACCAGGCAG AGAAAGGGAA CAATCCTTCG GGAAAGGGAA
AGGAGGGGGA GGTGGGGAAG GGTCTGAGGG CTTGGACACA
AGAAGAGCCG GAGGTGGCAG

RXRB rs2076310 C/T:
AGATGTGAAG CCACCAGTCT TAGGGGTCCG GGGCCTGCAC
TGTCCACCCC CTCCAGGTGG CCCTGGGGCT GGCAAACGGC
TATGTGCAAT CTGCGGGGAC AGAAGCTCAG GTATGTGGCT
CAGAGGATGA ACAGAGAGGG AGAGTCTGGG CCATGTATCA
C/T
CACCTGTGGG ATTCCCAGGG CTTATGGAGT TTGGTCAGAG
CAAGTGACCT GGGGGAGGCC TGATGGGAGT AAAGAAGCTG
AAGCTGAGAT GTAGGACGCG ATTGGGGGGA AGGTCAGAGG
GAAAAGGAAG CAGCGTGTAG GGTTTCTGAA CAGTGAGGAG
ACTGGGACTG GATCATCACT

BRD2 rs635688 C/T:
ATTTATTTAT TTTGTCCCAC AGTTTAATTG GGGCCGCAGT
TTAAGTAACT GTTCCTTTGA TGCATAGGGG GGGTGTGTGT
GTGTGTGTGT GTGTGTGAGA GTCGGGGATC GGTAGTCTCC
CTATAAGCAT TTATTTTTCT GTGGTTCTGA CCTAACATTT
C/T
TTTATTTAGG ATTATCACAA AATTATAAAA CAGCCTATGG
ACATGGGTAC TATTAAGAGG AGACTTGAAA ACAATTATTA
TTGGGCTGCT TCAGAGTGTA TGCAAGATTT TAATACCATG
TTCACCAACT GTTACATTTA CAACAAGGTG AGTTTTTCTG
TGTGTTCATT TAGTAGGTGG

HLA-DQA1 rs1142316 A/C:
TAACATCGAT CTAAAATCTC CATGGAAGCA ATAAATTCCC
TTTAAGAGAT
A/C
TATGTCAAAT TTTTCCATCT TTCATCCAGG GCTGACTGAA
ACCGTGGCTA

HLA-DRA rs7192 G/T:
CTTCTTCCCA CACTCATTAC CATGTACTCT GCCTTATTTC
CCCCCAGAGT TTGATGCTCC AAGCCCTCTC CCAGAGACTA
CAGAGAACGT GGTGTGTGCC CTGGGCCTGA CTGTGGGTCT
GGTGGGCATC ATTATTGGGA CCATCTTCAT CATCAAGGGA
G/T
TGCGCAAAAG CAATGCAGCA GAACGCAGGG GGCCTCTGTA
AGGCACATGG AGGTGAGTTA GGTGTGGTCA GAGGAAGACG
TATATGGAGA TATCTGAGGG AGGAAAACAG GGTGGGGAAA
GGAAATGTAA TGCATTTAAG AGACAAGGTA GGAACAGATG
TGGCTCTTGA TTTCTCTTTG

HSPA1B rs1061581 A/G:
CCAGGGCGAG GTTCGAGGAG CTGTGCTCCG ACCTGTTCCG
AAGCACCCTG GAGCCCGTGG AGAAGGCTCT GCGCGACGCC
AAGCTGGACA AGGCCCAGAT TCACGACCTG GTCCTGGTCG
GGGGCTCCAC CCGCATCCCC AAGGTGCAGA AGCTGCTGCA
A/G
GACTTCTTCA ACGGGCGCGA CCTGAACAAG AGCATCAACC
CCGACGAGGC TGTGGCCTAC GGGGCGGCGG TGCAGGCGGC
CATCCTGATG GGGGACAAGT CCGAGAACGT GCAGGACCTG
CTGCTGCTGG ACGTGGCTCC CCTGTCGCTG GGGCTGGAGA
CGGCCGGAGG CGTGATGACT

GTF2H4 rs3909130 A/G:
TTAAAATCTT CAAAGAACAG CTAAAAATTG ACAGAGCTTC
TTTATGGCAA ACTTTAGGTA AGGTTGAAAG ACAATTTACA
ATCTAGGAAG AAATGGTTGA TGAAATAAAC AAAATACAAA
AAGCTGTTAC AAAGCAATAA GAAAAAGAAA CATAATAGAA
A/G
GATTGGGACA GACCACTGCT TACTAGTTAG CCCTGCTCAG
CAAGGAGCAG CTTAAAAAAA AAAAAGAAG AAGAAAAGAA
```

TABLE 5-continued

Single Nucleotide Polymorphisms Found to
Predict Sex-Specific Prenatal Selection AAAGAAAAGA AAGAGGCCTG GCGGGGTGGC TCAGGCCTGT
AATCCCAACA CTTTGGGAGG CCAAAGAAGG TGGATCATTT
TAGCTCAGGA GTTCCAGACC HLA-E rs1264456 C/T:
CACAGGAAGA AATGGCAAAG TAAAAATTCA CACCCAGGAC
TCCCTGGGCT TTCTCACCGC ACATGTTGCC TTCTTACTGG
ATATCACCTG ACAGAATGAG ACTCAGGTGA TTACAGGGAT
TCACCAGGAA AACGGGAAAG TCGGCATGAC CAGAACTAGA
ACA
C/T
GGGCCAGTGA ATGCAGTTCT GGGTGGACCA TGGCATTGGA
AGCCAAAGGA TAGCTTGAAT GTGGTTAAAA AATTAAAACA
ACAAGGCACA AAACGCACAA ATGAAATACA AATGATGCTC
AAACACAGCT TTTATTTTAC TTCAAAGTTT ACCTCAGATC
AGCCTGGGAA GGTGAGGGGA HIST1H1T rs198844 C/G:
GTGACACTGA AAGGGCCTCG GTGATCAACT TGGACACAGA
GAGGTTCGGC ACTTTGCGAC TTGCACTTAT CAAGCCAGCC
GGCTTCCTCC CTCGCTTCTT GGTTGGAAGT TTCTCCATAG
CGGCTA
C/G
ACCAGCACTG GCAGAAGCTG CAGGCACGGT TTCAGACATA
ACAACAGAGA AACGCAAGAT GTAATAACCA GCGAAAAGCA
TGAAACACCC GGGCGGCCTC GGGGCCTTAT ATAGGGTAGG
GCGCGCTGTG ATTGGTGCAT CACCTAGGCA CCGCCCCCGC
CCCTTGGAGG AGGAGTATTT IRF4 rs12203592 C/T:
ATGTTTTGTG GAAGTGGAAG ATTTTGGAAG TAGTGCCTTA
TCATGTGAAA CCACAGGGCA GCTGATCTCT TCAGGCTTTC
TTGATGTGAA TGACAGCTTT GTTTCATCCA CTTTGGTGGG
TAAAAGAAGG
C/T
AAATTCCCCT GTGGTACTTT TGGTGCCAGG TTTAGCCATA
TGACGAAGCT TTACATAAAA CAGTACAAGT ATCTCCATTG
TCCTTTATGA TCCTCCATGA GTGTTTTCAC TTAGTCTGAT
GAAGGGTTCA CTCCAGTCTT TTCGGATGAT AAAATGCTTC
GGCTGTCAGT CTAATAAGGG IRF4 rs872071 A/G:
TGTTTTACAT GCCCCGTTTT TGAGACTGAT CTCGATGCAG
GTGGATCTCC TTGAGATCCT GATAGCCTGT TACAGGAATG
AAGTAAAGGT CAGTTTTTTT TTGTATTGAT TTTCACAGCT
TTGAGGAACA TGCATAAGAA ATGTAGCTGA AGTAGAGGGG
A/G
CGTGAGAGAA GGGCCAGGCC GGCAGGCCAA CCCTCCTCCA
ATGGAAATTC CCGTGTTGCT TCAAACTGAG ACAGATGGGA
CTTAACAGGC AATGGGGTCC ACTTCCCCCT CTTCAGCATC
CCCCGTACCC CACTTTCTGC TGAAAGAACT GCCAGCAGGT
AGGACCCCAG AGGCCCCCAA IFNG rs2069727 T/C:
TGTGGTATTT CTTTCCACTA GCATTTTGTT GGCTTTCGCT
TTTCCAGTTA GCAGCTCTTT GAATTATCTT TCTAAGATAC
AGATTTAATT ATGTCACTAT TCAATTCAGA GGTTCTGCTA
TGGAATGTAG TTTAAACTGC TTAGCTTGGC ACACAGAGAT
TTATTTCTAG CCCCTTCTCC ACCTTCCTAT TTCCTCCTTC
T/C
TTTCAGAATC TTCCTCTCCC TCATCCAATG CTGGCAAACA
CCAGTGGGGG TGGAGTAGTG GGTGTAAGCT CTAGGGAGAA
GGCTTGGATT GGAATCCAAG TTATTCCATT ACAAGTAGTG
TGACCTTTAA TACATTATGT ATATTGTCTA AGTTTCAGCT
TTATTGTCTG AAAAAGAAAA TP53 rs1042522 C/G:
TGAGGACCTG GTCCTCTGAC TGCTCTTTTC ACCCATCTAC
AGTCCCCCTT GCCGTCCCAA GCAATGGATG ATTTGATGCT
GTCCCCGGAC GATATTGAAC AATGGTTCAC TGAAGACCCA
GGTCCAGATG AAGCTCCCAG AATGCCAGAG GCTGCTCCCC
C/G
CGTGGCCCCT GCACCAGCAG CTCCTACACC GGCGGCCCCT
GCACCAGCCC CCTCCTGGCC CCTGTCATCT TCTGTCCCTT
CCCAGAAAAC CTACCAGGGC AGCTACGGTT TCCGTCTGGG
CTTCTTGCAT TCTGGGACAG CCAAGTCTGT GACTTGCACG
GTCAGTTGCC CTGAGGGGCT MDM2 rs2279744 G/T:
GGACTGGGGC TAGGCAGTCG CCGCCAGGGA GGAGGGCGGG
ATTTCGGACG GCTCTCGCGG CGGTGGGGGT GGGGGTGGTT
CGGAGGTCTC CGCGGGAGTT CAGGGTAAAG GTCACGGGGG
CCGGGGGCTG CGGGGCCGCT
G/T
CGGCGCGGGA GGTCCGGATG ATCGCAGGTG CCTGTCGGGT
CACTAGTGTG AACGCTGCGC GTAGTCTGGG CGGGATTGGG
CCGGTTCAGT GGGCAGGTTG ACTCAGCTTT TCCTCTTGAG
CTGGTCAAGT TCAGACACGT TCCGAAACTG CAGTAAAAGG
AGTTAAGTCC TGACTTGTCT KLRK1 rs10772266 A/G:
TGTTCATTCA ATATTATATT GGCTATGGGT TTGTCATAAA
TAGCTCTTAT CATTTTGAGA TATGTTCCAT CAATGCATAG
TTTGAGAGTG TTTTTTTTCT TTTTTTTTTT TAAGGCAAAT
GACAAATACC TAGTTTACC
A/G
TCTTTACTTT TTTAAACCTA ATGTTAACAT TAATATTTAA
ACAGTTGTCA AAAATTGCTA AGTTGCCAGC ATTCATGCAC
AACTAGAAAA CATCCTTAAC TTATCTTAAA CCAGAAATGT
ATTGCCATTA ATGCATTAAT ATCTTTTACT ACTAAATACT
GAAAAAAATT GAAATTATTT KLRK1 rs2617160 A/T:
ATGCAGGGGC ATCTATGGCC ACACCACCAT GATGCATCCA
GTCTCGTCTG GACACGCATG GGCATATTGA AGCAGAAGTG
AAATGATGAC TAATGTAAAA GTAAAAAAGT CTGCAAACAT
ATTTTAAGAA ATATGTATAT ATATATTTTC AGAACCTATT
TTCCATTCAG CTAGGTATTA
A/T
GTACTGGGCT ACACATACTG ACATATAATG TTAACTGGTG
TATTGTAATT ATATGAACTC AAGGCAGAGA TTCCATAAAT
CTGGAATTTA TACTTTGGGG AAAAACAGGT CATCATCTTG
GCAATTAATT AATTTTCTCT GGCACAGCTT CCTAAGCCAG
GAATGATTAA ATGATTTTTT KLRK1 rs2617171 C/G:
AAAATGACTT TTCTATAAAA ATAATGAGAT CTTTAAAACA
AATATTTTA AAGCCATTAG CATAAAACTT CACCATCTCT
TATAGTATTT GATCTAACCA CTTTCAAAAA TTAATTTGTT
TTTCTAAATA TTTTTTCTCT TAAAACATGT CTTTGAGTCA
TGAAATCAGA ATACATCTCT
C/G
TGTGTGTGTA TCATATATAC ATATATATTT AGTACACACA
AAAAAATAAA TGTTTTCTAC AATTATTCTG TTATTTATAA
ATTTGAAAAG TTCAGAAGCA GCATATTATC TTGGGGTTCA
GAGATATACA TTAAACAGAG AATTCTAATC CTCATTATTA
TGAAATGTTT CAAGGCGCTT

TABLE 6

Genotyping Methods for Each Single Nucleotide Polymorphism in The SNP Panel

| SNP | Genotyping Method | Detail |
|---|---|---|
| RXRB rs421446 C/T | Taqman allelic discrimination | ABI Cat No C__27015692_10 |
| RXRB rs2076310 C/T | Taqman allelic discrimination | ABI Cat No C__16167918_10 |
| BRD2 rs635688 C/T | Taqman allelic discrimination | ABI Cat No C__3213715_10 |
| HLA-DQA1 rs1142316 A/C | PCR-RFLP | BglII RFLP analysis |
| HLA-DRA rs7192 G/T | Taqman allelic discrimination | ABI Cat No C__8848630_20 |
| HSPA1B rs1061581 A/G | PCR-RFLP | PstI RFLP analysis |
| GTF2H4 rs3909130 A/G | Taqman allelic discrimination | ABI Cat No C__8941901_10 |
| HLA-E rs1264456 C/T | Taqman allelic discrimination | ABI Cat No C__8942134_10 |
| HIST1H1T rs198844 G/C | Taqman allelic discrimination | ABI Cat No C__3266627_10 |
| IRF4 rs12203592 C/T | Taqman allelic discrimination | ABI Cat No C__31918199_10 |
| IRF4 rs872071 A/G | Taqman allelic discrimination | ABI Cat No C__8770093_10 |
| LIF rs929271 | Taqman allelic discrimination | ABI Cat No C__7545904_10 |
| TP53 rs1042522 G/C | Taqman allelic discrimination | ABI Cat No C__2403545_10 |
| MDM2 rs2279744 T/G | PCR-RFLP | MspA1I RFLP analysis |
| SLC11A2 rs422982 | Taqman allelic discrimination | ABI Cat No C__570333_10 |
| SLC40A1 rs1439814 | Taqman allelic discrimination | ABI Cat No C__2108641_10 |
| RRM2 rs1130609 | Taqman allelic discrimination | ABI Cat No C__379242_20 |
| TMPRSS6 rs733655 T/C | Taqman allelic discrimination | ABI Cat No C__3289858_1_ |
| HMOX1 rs2071748 G/A | Taqman allelic discrimination | ABI Cat No C__2469922_1_ |
| IFNG rs2069727 T/C | Taqman allelic discrimination | ABI Cat No C__2683475_10 |
| IL6 rs1800796 G/C | Taqman allelic discrimination | ABI Cat No C__11326893_10 |
| KLRK1 rs10772266 A/G | Taqman allelic discrimination | ABI Cat No C__9345268_10 |
| KLRK1 rs2617160 T/A | Taqman allelic discrimination | ABI Cat No C__1841959_10 |
| KLRK1 rs2617171 G/C | Taqman allelic discrimination | ABI Cat No C__26984346_10 |

What is claimed is:

1. A method for predicting prenatal loss of a male conceptus or embryo, comprising the steps of:
(a) providing a biological sample from a pregnant woman;
(b) isolating a nucleic acid from said biological sample;
(c) performing a polymerase chain reaction (PCR) on said isolated nucleic acid to produce an amplicon;
(d) assessing said amplicon for the presence of adenine (A) at SNP GTF2H4 rs3909130; and
(e) predicting an increased risk of prenatal loss of said male conceptus or embryo in said pregnant woman by said presence of adenine (A) at said SNP GTF2H4 rs3909130,
wherein the presence of said adenine (A) at said SNP GTF2H4 rs3909130 is indicative of an increased risk of prenatal loss of said male conceptus or embryo.

2. The method of claim 1, wherein said biological sample is derived from a conceptus or amniocentesis.

3. The method of claim 1, wherein said nucleic acid is selected from the group consisting of genomic DNA, and isolated DNA.

4. The method of claim 1, wherein said assessing step is performed by polymerase chain reaction-restriction fragment length polymorphism assay or TaqMan allelic discrimination assay.

5. The method of claim 4, wherein said assessing step is performed by polymerase chain reaction-restriction fragment length polymorphism assay.

6. The method of claim 4, wherein said assessing step is performed by TaqMan allelic discrimination assay.

7. The method of claim 1, wherein said assessing step is performed by a process which comprises subjecting said isolated nucleic acid to a PCR flanking the region of said SNP.

8. The method of claim 1, wherein said assessing step is performed on the presence of a SNP further selected from the group consisting of RXRB rs421446, BRD2 rs635688, HLA-E rs1264456, IRF4 rs12203592, IRF4 rs872071, LIF rs929271, TP53 rs1042522, MDM2 rs2279744, SLC11A2 rs422982, SLC40A1 rs1439814, and RRM2 rs1130609.

9. A method of predicting prenatal survival probability of a prospective male offspring of a couple, comprising the steps of:
(a) providing a biological sample from a pregnant woman;
(b) isolating nucleic acid from said biological sample;
(c) performing a polymerase chain reaction (PCR) on said isolated nucleic acid to produce an amplicon;
(d) assessing said amplicon for the presence of adenine (A) at SNP GTF2H4 rs3909130; and
(e) predicting a decreased prenatal survival probability of said prospective male offspring of said couple by said presence of adenine (A) at said SNP GTF2H4 rs3909130,
wherein the presence of said adenine (A) at said SNP GTF2H4 rs3909130 is indicative of a decreased prenatal survival probability of said prospective male offspring.

10. The method of claim 9, wherein said assessing step is performed on the presence of a SNP further selected from the group consisting of RXRB rs421446, BRD2 rs635688, HLA-E rs1264456, IRF4 rs12203592, IRF4 rs872071, LIF rs929271, TP53 rs1042522, MDM2 rs2279744, SLC11A2 rs422982, SLC40A1 rs1439814, and RRM2 rs1130609.

11. The method of claim 9, wherein said biological sample is derived from a conceptus or amniocentesis.

12. The method of claim 9, wherein said nucleic acid is selected from the group consisting of genomic DNA, and isolated DNA.

13. The method of claim 9, wherein said assessing step is performed by polymerase chain reaction-restriction fragment length polymorphism assay or TaqMan allelic discrimination assay.

14. The method of claim 9, wherein said assessing step is performed by polymerase chain reaction-restriction fragment length polymorphism assay.

15. The method of claim 9, wherein said assessing step is performed by TaqMan allelic discrimination assay.

16. The method of claim 9, wherein said assessing step is performed by a process which comprises subjecting said isolated nucleic acid to a PCR flanking the region of said SNP.

* * * * *

```
                          SEQUENCE LISTING

<160> NUMBER OF SEQ ID NOS: 6

<210> SEQ ID NO 1
<211> LENGTH: 20
<212> TYPE: DNA
<213> ORGANISM: Homo sapiens

<400> SEQUENCE: 1
catcgacttc tacacgtcca                                              20

<210> SEQ ID NO 2
<211> LENGTH: 20
<212> TYPE: DNA
<213> ORGANISM: Homo sapiens

<400> SEQUENCE: 2
caaagtcctt gagtcccaac                                              20

<210> SEQ ID NO 3
<211> LENGTH: 23
<212> TYPE: DNA
<213> ORGANISM: Homo sapiens

<400> SEQUENCE: 3
caagggccat tgtgaatcyc cat                                          23

<210> SEQ ID NO 4
<211> LENGTH: 16
<212> TYPE: DNA
<213> ORGANISM: Homo sapiens

<400> SEQUENCE: 4
tgggyggcar tgccaa                                                  16

<210> SEQ ID NO 5
```

-continued

```
<211> LENGTH: 20
<212> TYPE: DNA
<213> ORGANISM: Homo sapiens

<400> SEQUENCE: 5
cgggagttca gggtaaaggt                                              20

<210> SEQ ID NO 6
<211> LENGTH: 20
<212> TYPE: DNA
<213> ORGANISM: Homo sapiens

<400> SEQUENCE: 6
agcaagtcgg tgcttacctg                                              20
```